United States Patent
Kanduri et al.

(10) Patent No.: US 11,306,311 B2
(45) Date of Patent: Apr. 19, 2022

(54) LONG NON-CODING RNA IN CANCER

(71) Applicants: Chandrasekhar Kanduri, Mölndal (SE); Mohamad Moustafa Mahmoud Ali, Gothenburg (SE); Luisa Statello, Gothenburg (SE); Vijay Suresh Akhade, Gothenburg (SE); Santhilal Subhash, Gothenburg (SE); Subazini Thankaswamy Kosalai, Västra Frölunda (SE)

(72) Inventors: Chandrasekhar Kanduri, Mölndal (SE); Mohamad Moustafa Mahmoud Ali, Gothenburg (SE); Luisa Statello, Gothenburg (SE); Vijay Suresh Akhade, Gothenburg (SE); Santhilal Subhash, Gothenburg (SE); Subazini Thankaswamy Kosalai, Västra Frölunda (SE)

(*) Notice: Subject to any disclaimer, the term of this patent is extended or adjusted under 35 U.S.C. 154(b) by 0 days.

(21) Appl. No.: 16/620,700

(22) PCT Filed: Jun. 8, 2018

(86) PCT No.: PCT/EP2018/065210
§ 371 (c)(1),
(2) Date: Dec. 9, 2019

(87) PCT Pub. No.: WO2018/224668
PCT Pub. Date: Dec. 13, 2018

(65) Prior Publication Data
US 2020/0140861 A1   May 7, 2020

(30) Foreign Application Priority Data
Jun. 8, 2017   (SE) .................................. 1750724-5

(51) Int. Cl.
| | | |
|---|---|---|
| *C12N 15/113* | (2010.01) | |
| *A61P 35/00* | (2006.01) | |
| *C12Q 1/6886* | (2018.01) | |
| *C12Q 1/68* | (2018.01) | |
| *C12N 15/11* | (2006.01) | |

(52) U.S. Cl.
CPC ........... *C12N 15/113* (2013.01); *A61P 35/00* (2018.01); *C12N 15/111* (2013.01); *C12Q 1/68* (2013.01); *C12Q 1/6886* (2013.01); *C12N 2310/113* (2013.01); *C12N 2310/14* (2013.01); *C12N 2310/531* (2013.01); *C12Q 2600/158* (2013.01)

(58) Field of Classification Search
CPC ................ C12N 15/113; C12N 15/111; C12N 2310/113; C12N 2310/14; C12N 2310/531; A61P 35/00; C12Q 2600/158
See application file for complete search history.

(56) References Cited

U.S. PATENT DOCUMENTS

2018/0305689 A1 * 10/2018 Saetrom .................. A61P 35/00

FOREIGN PATENT DOCUMENTS

| WO | 2012/149522 A1 | 11/2012 | |
|---|---|---|---|
| WO | WO-2012149522 A1 * | 11/2012 | ........... C12Q 1/6886 |

OTHER PUBLICATIONS

Kannan, K. et al., Recurrent chimeric RNAs enriched in human prostate cancer identified by deep sequencing , Proceedings of the National Academy of Sciences, 108(22): 9172-9177, May 12, 2011.
Kannan, K. et al., Recurrent chimeric RNAs enriched in human prostate cancer identified by deep sequencing , Proceedings of the National Academy of Sciences, 108(22): 9172-9177, May 12, 2011, Supplemental online data retrieved from the internet May 31, 2011, 25 pages.
Ali, M. et al., PAN-cancer analysis of S-phase enriched lncRNAs identifies oncogenic drivers and biomarkers, Nature Communications, 9(1):883, Feb. 28, 2018, 20 pages.
Rao, A. et al., Perspectives of long non-coding RNAs in cancer, Molecular Biology Reports, 44(2): 203-218, Apr. 8, 2017.

* cited by examiner

*Primary Examiner* — J. E. Angell
(74) *Attorney, Agent, or Firm* — Julie K. Staple; Dinsmore & Shohl LLP

(57) ABSTRACT

There are provided polynucleotides that is able to bind to and inhibit the long non coding RNA transcript SCAT7. These polynucleotides can be used for the treatment of cancer. Expression analysis of SCAT7 can be used for diagnosis of cancer.

8 Claims, 13 Drawing Sheets
Specification includes a Sequence Listing.

LONG NON-CODING RNA IN CANCER

FIELD OF THE INVENTION

This invention relates to a non-coding RNA transcript identified in humans and its use in cancer treatment and diagnosis, in particular a polynucleotide that is at least partially complementary to the non-coding RNA transcript.

BACKGROUND

Protein-coding genes are small islands in the vast genetic information carefully replicated from generation to generation. Whereas protein-coding genes have been the subject of intense research since the 1960s, non-coding DNA is only beginning to be understood recently. Non-coding DNA may be transcribed into RNA just like protein coding DNA, but forming non-coding RNA instead of coding-mRNA.

One form of non-coding RNA transcripts is long non-coding RNA (lncRNA), which are non-coding transcripts with a length of more than 200 base pairs. The transcription level of lncRNAs if often well below that of mRNA.

The role and properties of lncRNAs is only beginning to be elucidated. It is thought that lncRNAs have a role in regulating expression of protein-coding genes.

Cancer is a major cause of death in the western world. Although the treatment of cancer has steadily improved, there is still a great need for improved treatment of this disease. There is also a need for improved diagnosis of cancer.

The lncRNA transcript SCAT7 (ELF3-AS1) has previously been identified. However, the biological role of this transcript has not been understood. Here we provide new treatment and diagnosis involving this lncRNA.

SUMMARY OF THE INVENTION

In a first aspect of the invention there is provided a polynucleotide that is able to bind to and inhibit a long non-coding RNA transcript that comprises the nucleotide sequence of SEQ ID NO 3. In particular there is provided a polynucleotide that is able to bind to and inhibit a long non-coding RNA transcript that comprises or consists of the sequence SEQ ID NO 1 or SEQ ID NO 2. Preferably the long coding RNA comprises or consists of the sequence SEQ ID NO 1 (SCAT7-L) or SEQ ID NO 2 (SCAT7-S). In a preferred embodiment the polynucleotide binds and inhibits a long non-coding RNA that comprises or consists of the sequence of SEQ ID NO 1 (SCAT7-L). The polynucleotide may bind to a selected part of SEQ ID NO 3. The polynucleotide may bind for example a sequence selected from SEQ ID NO 14 to SEQ ID NO 20.

Suitable polynucleotides are for example a DNA polynucleotide, for example a gapmer, selected from SEQ ID NO 4 and SEQ ID NO 5, a shRNA polynucleotide selected from SEQ ID NO 6 and SEQ ID NO 7, or a siRNA polynucleotide which is a duplex of SEQ ID NO 8 and SEQ ID NO 9, a duplex of SEQ ID NO 10 and SEQ ID NO 11 or a duplex of SEQ ID NO 12 and SEQ ID NO 13.

In a second aspect of the invention there is provided a polynucleotide according to the first aspect of the invention for use in the treatment of a disease. In a preferred embodiment the disease is cancer, more preferably a cancer selected from the group consisting of lung cancer, liver cancer, kidney cancer, bladder cancer, breast cancer, prostate cancer and endometrial cancer. The cancer may be a cancer that is resistant against chemotherapy, such as resistant to a platinum-based chemotherapeutic agent.

In a third aspect of the invention there is provided a pharmaceutical composition comprising a polynucleotide according to the first aspect of the invention.

In a fourth aspect of the invention there is provided a method for treatment comprising administering to a patient a polynucleotide according to the first aspect of the invention.

In a fifth aspect of the invention there is provided a polynucleotide that detects the lncRNA of SEQ ID NO 1 or SEQ ID NO 2 for use in diagnosis. In a preferred embodiment the diagnosis is diagnosis of cancer, more preferably kidney cancer or liver cancer.

In a sixth aspect of the invention there is provided a method for diagnosis comprising detecting an RNA transcript comprising SEQ ID NO 3, SEQ ID NO 1 or SEQ ID NO 2 in a sample of a patient.

In a seventh aspect of the invention there is provided a polynucleotide comprising or consisting of a sequence selected from the group consisting of SEQ ID NO 4-SEQ ID NO 13.

In an eighth aspect of the invention there is provided the use of the polynucleotides above, in life science research. In a preferred embodiment the life science research is the function of the SCAT7 transcript.

DETAILED DESCRIPTION

Abbreviations

Figure 1:
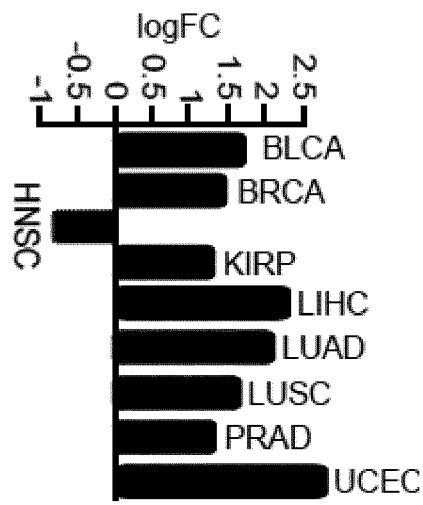
FIG. 1 is a bar graph showing the significant differential expression levels of SCAT7 expressed as log 2 fold change across different cancer types obtained from TCGA datasets.

KIRC—Kidney renal cell cancer
Csh—Control Short Hairpin
Sh—Short Hairpin
LNA—Locked Nucleic Acid Sometimes it is referred to an interval of sequences herein. This refers to all the sequences in the interval including endpoint, thus for example "SEQ ID NO 2 to SEQ ID 5" refers to SEQ ID NO, 2, 3, 4, and 5. Sequence information is provided from 5' end to 3' end.

A sequence herein may also comprise a substantially similar sequence. A "substantially similar" sequence preferably has at least 80%, more preferably 90%, more preferably 95%, more preferably 98% and most preferably 99% sequence similarity to the described sequences. Sequence similarity can be analysed using for example BLAST2 sequences, using standard settings. Such sequences preferably have substantially the same properties as the sequences described herein. One example of such sequence variations may be for example polymorphisms in the human population in the SCAT7 sequence. For example, point mutations, leading to the replacement of one base with another, deletions or insertions, are examples of such polymorphisms. Thus, SEQ ID NO 1, 2 and 3 also comprises sequences with 5, more preferably 4, more preferably 3, more preferably 2 and most preferably 1 base substitution or base deletion, or base insertions. For SEQ ID NO 4-13, the sequence may have 2, more preferably 1 substitutions.

Aspects of the invention relates to polynucleotide molecules. Useful protocols involving polynucleotides molecules can be found in Ausubel F M et al, Current Protocols in Molecular Biology (Wiley) and Sambrook, Molecular Cloning: a Laboratory Manual, (Cold Spring Harbour) (Current editions). These publications can be useful for the various aspects of the invention described herein.

Generally, the polynucleotide described herein is able to bind to and inhibit the SCAT7 long transcript (SCAT7-L, SEQ ID NO 1) and the SCAT7 short transcript (SCAT7-S, SEQ ID NO 2). In various embodiments it may be desirable to target the SCAT7-L or the SCAT7-S transcript specifically. The SCAT7-S and the SCAT7-L share a common core sequence (SEQ ID NO 3). Targeting this common sequence may be used to knock down both SCART7-L and SCART7-S, when both transcripts are present. The SCAT7-L and the SCAT7-S transcript are collectively referred to as "SCAT7" herein. As the case may be, the "target transcript" refers to SCAT7-L, SCAT7-S or both.

The sequence of the SCAT7-L (SEQ ID NO 1) transcript is as follows (788 base pairs). T

```
SEQ ID NO 1:
cacgggcac uggccugggc agguggcggg aacguugcug gggugggcau cugugcuuuc ggcugcccuc uggcccagga aauuccuccc aggggccagg ccagagaugg gccaggcagg gggagggcaa gugagggaac augaacccu ggcugaccug agucagaaag cugcuggcc cuaaauucca gagauucagc aacaaagagg ccuaguaggg agaggaguua cuagguuuag ggguuuuucc cagaacaccc aggacucugg ccaggggcug gaaggugcuc caggcucaau gcugggcaau acucauggau uaauuggugc uggcugggcc ugccagccua gucguggccc caggguccc acuaaagggc uccuucucca gcgcccacuc uguuggcaag gucuucacua ccaucaccug ccuggacucc auccaagcau caggguugcu gcagucgcuc cugaagagac ccggcucugc uugaaaguuc uucccucagc gccugcugga gcccucccug ccggaguugc cagaauccac acggaaucca cagaucugcc cugaugauca ugaaggaaug cgaaagagcc ugguaaaacg auauggacuu gugcaaaugc aaagcaaugg ugaagucauc acgaaccgca cagacuggac agaacuccua ucuggcugca auggcuuggg uucagucagc ccagggcca gagaauuggc uacaaagagc ucuggagugc cccucccucc aauaaagua uucuaagcgu gcacugau
```

The part of the sequence which is identical to SCAT7-S is underlined and referred to as SEQ ID NO 3 below.

The sequence of the SCAT7-S transcript (500 base pairs) is as follows, and the overlapping part (SEQ ID NO 3) that is present in SCAT-7 is underlined:

```
SEQ ID NO 2:
aagagaucag aaucagcuu ccccagggac agcaaggcca agaagguguc cagauccugg ccucucucca gaucuuggac ucucucaagg ccaagacucu cucucuuaag aucucuaucu caaggccaag aucucucucc agauauuggc cucucucaag guacuuccaa gaucucagag ggccauucac uguggaucua auaugaagac agagaaacca gccuuccaga ggagcggaca cauuuccuua gucccaggau acacuuugug uggaauccac agaucugcc ugaugaucau gaaggaaugc gaaagagccu gguaaaacga uauggacuug ugcaaaugca aagcaauggu
```

-continued
```
gaagucauca cgaaccgcac agacuggaca gaacuccuau cuggcugcaa uggcuugggu ucagucagcc cagggccag agaauuggcu acaaagagcu cuggagugcc ccucccucca aauaaaguau ucuaagcgug
```

The overlapping sequence (SEQ ID NO 3) between SCAT7-L and SCAT7-2 is the following sequence:

```
                                      SEQ ID NO 3
ggaauccac agaucugccc ugaugaucau gaaggaaugc gaaagagccu gguaaaacga uauggacuug ugcaaaugca aagcaauggu gaagucauca cgaaccgcac agacuggaca gaacuccuau cuggcugcaa uggcuuggu ucagucagcc cagggccag agaauuggcu acaaagagcu cuggagugcc ccucccucca aauaaaguau ucuaagcgug
```

In one embodiment SCAT7-L and not SCAT7-S is specifically targeted. This may be done by directing a polynucleotide to the SCAT7-L sequence (SEQ ID NO 1) part that is not present in SCAT7-S (SEQ ID NO 2).

In a similar manner, specific targeting SCAT7-S but not SCAT7-L may be done by using the sequence part of SEQ ID NO 2 that is not present in SEQ ID NO 1.

In one embodiment both SCAT7-L and SCAT7-S are targeted, for example by targeting SEQ ID NO 3. In one embodiment, SCAT7-L is targeted by targeting SEQ ID NO 1.

In preferred embodiments the polynucleotide binds to a target sequence selected from SEQ ID NO 14 to SEQ ID NO 20, or a part of such a sequence, the part being at least 8, more preferably 9, 10, 11, 12, 13, 14, 15, 16, 17, 18, 19, 20 or most preferably at least 21 consecutive nucleotides of such a sequence.

The SCAT7-L or the SCAT7-S transcript may be inhibited using any suitable technology that renders a RNA transcript (the "target transcript") inactive. The target transcript can be made inactive by for example causing its degradation or sequestering it, changing its subcellular location or making it unable to bind to other molecules, for example by blocking hybridization. Such technologies are usually referred to as "knockdown" technologies. A knock-down technology is a technology that utilizes a polynucleotide that is at least partially complementary to the target transcript, and that renders the target transcript non-functional, for example by causing the breakdown of the target transcript or by sequestering the transcript or changing the subcellular location of the transcript or making the transcript unable to bind to other molecules. As the skilled person knows, there are many different useful knockdown technologies. They all involve using a polynucleotide sequence which is at least partially complementary to the target sequence. The length of the polynucleotide is chosen dependent on the technology used (for example RNAi or antisense) but should at least have a length such that it is specific for the target transcript (given the size of the human genome and the fact that the genetic code contains four information "bits": C, G, A and T/U). Usually a length of at least 16, more preferably 17, even more preferably 18, even more preferably 19, even more preferably 20 and most preferably at least 21 nucleotides is enough to provide specificity and stable binding. Very long polynucleotides may be avoided since they are more difficult to produce and cumbersome in drug delivery. An upper limit of the length of the polynucleotide may be 80 nucleotides, where 60 is more preferred, 40 is even more preferred and 30 is most preferred.

A preferred method for inhibiting the target transcript is using the RNA interference pathway (RNAi), for example by using siRNA or shRNA. Briefly, the RNAi pathway involves the binding of short complementary RNA molecules to the target transcript, together with endogenous proteins that inhibits the target transcript by for example catalysing the breakdown of the target transcript. Another preferred method is the recruitment of RNAse H.

The polynucleotide used herein can contain the bases cytosine (C), guanine (G), adenine (A) thymidine (T), or uracil (U). The skilled person knows that these bases can be replaced, in one or more positions in an otherwise complementary sequence, with other purines or pyrimidines, for example inosine.

In a similar manner, a polynucleotide may comprise modified nucleotides, such as, for example, locked nucleic acids. A locked nucleic acid is a nucleic acid modified by adding a methylene bridge between the 2' oxygen and the 4' carbon (Kurreck J, et al Nucleic Acids Res. 2002 May 1; 30 (9):1911-8).

Other modifications that can be used are well known to the person skilled in the art. Such modifications may be used to enhance or enable for example detection, purification, stability, drug delivery, targeting or binding specificity or another desirable property of the polynucleotide. It is referred to Beaucage, S L et a,l Current protocols in nucleic acid chemistry, John Wiley and sons, for more information about modified nucleotides.

The polynucleotide may also be conjugated to other types of molecules for example antibodies or other proteins, lipids, carbohydrates, polymers or other types of molecules. Such conjugation may be used to enhance or enable for example detection, purification, stability, drug delivery, targeting or binding specificity or another desirable property of the polynucleotide. One example of such a conjugate is a dynamic poly conjugate (DPC) which comprises a membrane-disrupting polymer useful for delivering the polynucleotide into the cell. Conjugation can be done using covalent or non-covalent bonding. Examples of non-covalent conjugation systems include the biotin-streptavidin system.

The polynucleotide is preferably complementary to the target sequence (i.e. a part of SEQ ID NO 1, SEQ ID NO 2 or SEQ ID NO 3) and able to form a duplex with the target sequence by hybridization. Accordingly, the polynucleotide is able to bind to the target sequence by hybridization. Preferably the polynucleotide used in knockdown is able to at least partially hybridize with the target transcript. For example, the polynucleotide may comprise a selection of 14, 15, 16 or more (or other suitable number) of the reverse complementary sequences of one of SEQ ID NO 1, SEQ ID NO 2 or SEQ ID NO 3, or a sequence that is substantially similar to such a sequence.

A useful starting point for designing the polynucleotide may be selecting a part of SEQ ID NO 1, SEQ ID NO 2 or SEQ ID NO 3 as a target sequence and creating its reverse complement sequence. This is easily done using on-line bioinformatics tools. The reverse complement sequence if SEQ ID NO 1 is SEQ ID NO 21, the reverse complement sequence of SEQ ID NO 2 is SEQ ID NO 22 and the reverse complement sequence of SEQ ID NO 3 is SEQ ID NO 23. Thus, the polynucleotide will typically comprise a part of SEQ ID NO 21, 22 or 23. When the nucleotide is DNA there will off course be T instead if an U.

The duplex may be formed under what the skilled person refers to as stringent conditions or may be in more physiologically relevant conditions. A complementary polynucleotide may be completely complementary or partially complementary for example by comprising G:U wobble or having one or more nucleotides that is not involved in Watson-Crick base pairing with the target sequence. It may be preferred that the polynucleotide contains at most 3 mismatching nucleotides. The polynucleotide may have an overhang that does not hybridize with the target sequence.

The polynucleotide can be manufactured by organic synthesis methods known in the art. Alternatively the polynucleotides can be produced by using a vector, for example a plasmid as is known in the art. The plasmid can be used to produce the polynucleotide in vitro, and the polynucleotide can then be purified from the culture. Suitable hosts include E. coli, CHO cells, yeast, plant cells etc.

Alternatively, the polynucleotide can be produced in the subject, the target cell or target animal by introducing an expression vector into cells of the subject or animal as known in the art of gene therapy.

One suitable vector for production of shRNA is used is pLKO.1-TRC. This plasmid can be introduced into cells via direct transfection or can be converted into lentiviral particles for subsequent transduction of a target cell line.

siRNA

One method for knocking down RNA transcripts that has been extensively studied is the use of siRNA, which depends on the above-mentioned RNAi pathway. siRNA involves the administration of double stranded RNA (dsRNA) where one strand is complementary to the target transcript. When the siRNA has entered the cell it is separated into the passenger strand (which is degraded) and the guide strand which is the strand that is complementary to the target sequence. The guide strand is incorporated into a protein complex called RISC. The RISC complex together with the protein argonaute catalyses the breakdown of the target transcript.

The length of the siRNA duplex structure may be from 15 to 30 base pairs, more preferably from 18 to 25, more preferably from 19 to 24 base pairs and most preferably from 19 to 21 base pairs. Similarly the region of complementarity to the target sequence is preferably from 15 to 30 base pairs, more preferably from 18 to 25 more preferably from 19 to 24 base pairs and most preferably from 19 to 21 base pairs. The duplex preferably has nucleotide overhangs at the 3'-ends. The overhang is preferably from 1 to 4 nucleotides, preferably 2 nucleotides long. The overhang nucleotide is preferably T most preferably TT (and not U or UU).

The skilled person knows how to design useful siRNA for activating the RNAi pathway. Examples of useful rules include: 1) the guide strand of the siRNA duplex preferably binds to a sequence that begins with AA, 2) A C+G content of at most 30-50% is preferred, 3) stretches of >4 T's or A's in the target sequence is to be avoided, 4) sequences that share homology with other parts of the human genome should be avoided. BLAST can be used to analyse this within seconds. There are several web tools that aid in designing siRNAs.

See also the following references for design of polynucleotides: Elbashir, et al. (2001) EMBO J 20: 6877-6888, Brown, et al. (2002) Ambion TechNotes 9 (1): 3-5, Sui, G., et al. Proc. Natl. Acad. Sci. USA 99 (8): 5515-5520, Lee, N. S., et al Nature Biotechnology 20: 500-505, Yu, J.-Y., et al Proc. Natl. Acad. Sci. USA 99 (9): 6047-6052, Paul, C. P., et al. Nature Biotechnology 20: 505-508, Brummelkamp, T. R., et al Science 296: 550-553, Jacque, J.-M., et al Nature 418: 435-438, Miyagishi, M. and Taira, K. (2002) Nature Biotechnology 20: 497-500, Paddison, P. J., et al Genes Devel. 16: 948-958 Elbashir S M, et al Nature. 2001 May 24; 411 (6836):494-8.

Non-limiting examples of suitable siRNA polynucleotides are SEQ ID NO 8 in duplex with a suitable hybridization partner such as SEQ ID NO 9, SEQ ID NO 11 in duplex with a suitable hybridization partner such as SEQ ID NO 10 and SEQ ID NO 13 in duplex with a suitable hybridization partner such as SEQ ID NO 12. A suitable hybridization partner is a polynucleotide sequence that is capable of forming a stable duplex with its partner, by being at least partially complementary.

Non-limiting examples of suitable target sequences for siRNA are SEQ ID NO 18 to SEQ ID NO 20.

shRNA

Another useful method for knocking down the SCAT7 transcript is the use of short hairpin RNA (shRNA) which mimics the natural microRNA (miRNA) pathway, which involves the RISC complex in a manner similar to siRNA. shRNA is formed by short stretches of RNA that folds back and at least partially base pairs with itself, thus forming a hairpin-like structure. The hairpin is cleaved once in the cell, resulting in a duplex molecule. One strand of the duplex molecule serves as the guide strand for the RISC complex. shRNA can be obtained by transcription from DNA that is complementary to the desired shRNA molecule. A useful vector is the abovementioned pLKO.1-TRC vector. Non-limiting examples of suitable shRNA polynucleotides are SEQ ID NO 6 and SEQ ID NO 7. Non-limiting examples of suitable target sequences of shRNA are SEQ ID NO 16 and SEQ ID NO 17.

Antisense Oligonucleotides

Yet another useful approach is the use of antisense oligonucleotides. This approach uses the fact that RNase H specifically degrades RNA:DNA complexes. Thus by administering a DNA strand that binds to the SCAT7 transcript, the RNAse H enzyme will degrade SCAT7. This pathway may be recruited by using, for example, so called GapmeRs. GapmeRs are DNA polynucleotides with short stretches of modified nucleic acids, for example locked nucleic acids (LNAs) at the ends. GapmeRs with other types of modifications than LNA are discussed in Kasuya et al. Sci Rep. (2016) July 27; 6:30377. GapmeRs are useful because they increase the binding strength of the polynucleotide to the target sequence.

GapmeRs have a central portion of unmodified nucleotides flanked by a number of modified nucleic acids, for example LNAs, on each side. Preferably the LNAs participate in hybridization. The number of unmodified nucleotides can be from 6 to 15, more preferably from 6 to 12, even more preferably from 7 to 10. The number of LNAs on each side of the unmodified part is preferably from 1 to 6 more preferably 2 to 4 and most preferably 3. In a preferred embodiment, the number of central unmodified nucleotides is 10 and there are 3 LNAs on each side. The GapmeR may have a modified backbone to include phosphothioate, which enhances pharmacokinetics and pharmacodynamics of the nucleotide. Methods for designing GapmeRs which are antisense molecules containing locked nucleic acids are described in Kurreck J, et al Nucleic Acids Res. 2002 May 1; 30 (9):1911-8. GapmeRs are available from, for example, Exiqon A/S.

Non-limiting examples of suitable DNA sequences are SEQ ID NO 4 and SEQ ID NO 5. Non-limiting examples of suitable target sequences for antisense oligonucleotides are SEQ ID NO 14 and SEQ ID NO 15.

A polynucleotide can be analysed for ability to bind to and inhibit the SCAT7 transcript by methods known in the art within days. A simple way to confirm binding of the polynucleotide to the target sequence is to allow the polynucleotide to bind to the target sequence in vitro. One suitable method which is time and cost efficient is to test the candidate polynucleotide on cultured cells known to express SCAT7. The expression of the target transcript can be analysed using any suitable method, including rt-qPCR, northern blot, in situ hybridization or hybridization microarrays. A particularly suitable method is RT-qPCR. The polynucleotide is administered to the cultured cells and expression of the target transcript is compared to non-treated or mock treated cells. Administration to cultured cells can be carried with for example liposomes and/or electroporation as is known in the art. One useful transfection reagent for this purpose is Lipofecatamine from ThermoFisher. Suitably transient transfection is used. A suitable time point for measuring inhibition is 48 hours post transfection.

The degree of inhibition can be measured as the decrease of the presence of SCAT7 transcript. The degree of inhibition is usually expressed in terms of the formula $$\text{Inhibition} = \frac{(mRNA \in controlcells) - (mRNA \in \text{treated cells})}{(mRNA \in \text{control cells})} \times 100$$

Expression of the target transcript may inhibited be at least 10%, 20%, 30%, 40%, 50%, 60%, 70%, 85%, 90%, 95% or most preferably at least 99%.

Knockdown efficiency can also be measured by measuring a parameter that is affected by SCAT7 such as proliferation, senescence, migration, colony formation, cell cycle, apoptosis, or signalling trough FGFR2, FGFR3 PI3K/AKT or Ras/MAPK.

Animal studies can also be used for confirming the activity of the polynucleotide. Accordingly, the polynucleotides can be administered to animals and the effect can be measured as is known in the art. For example, the effect of tumour formation or tumour growth can be measured by using a mouse tumour model, for example a subcutaneous mouse tumour model. Suitably a tumour cell line is used in mice that allow the growth of such tumour cells (for example SCID mice). The polynucleotides being tested can be administered and formulated as described herein and as is known to the person skilled in the art. For example, siRNA molecules can be administered to animals using liposomes with high efficiency (Eguchi et al, J Hepatol. 2016 March; 64 (3):699-707).

Pharmaceutical Composition

When used in therapy, the polynucleotides are preferably administered to the patient in the form of a pharmaceutical composition. Such a pharmaceutical composition comprises an effective amount of the polynucleotide and a pharmaceutically acceptable carrier, which typically is an aqueous or non-aqueous solution comprising a variety of different pharmacologically acceptable compounds. The formulation is made to suit the mode of administration. There is a wide variety of possible formulations. The formulation may be adapted to increase the uptake or stability of the polynucleotide or to improve the pharmacokinetics or pharmacodynamics of the polynucleotide, or to enhance other desirable properties of the formulation.

In general, methods of formulating pharmaceutical compositions comprising nucleic acids are well known in the art. Administered siRNA have been used for therapeutic silencing of genes (Soutschek, et al., Nature 432, 173-178 (2004)). siRNA molecules can be administered to animals using liposomes with high efficiency (Eguchi et al, J Hepatol. 2016 March; 64 (3):699-707). Administration of GapmeRs to animals is described in for example Kasuya et al. Sci Rep. (2016) Jul. 27; 6:30377. Formulations of the GapmeR drug mipomersen is described in U.S. Pat. No. 7,407,943. Various methods can be used to facilitate uptake of polynucleotides by cells. Such methods include liposomes, bacteria, the use of PEGylation, cyclodextrin polymer nanoparticles (CDP) or cholesterol. A review of delivery systems for siRNA can be found in Kanasty et al, Nat Mater. 2013 November; 12 (11):967-77. Wittrup & Lieberman, Nature Reviews Genetics, Vol. 16, 543-552 (2015) is also a useful review of the field.

Formulation for parenteral administration such as for example intraarticular, intravenous, intradermal, intraperitoneal, intratumoural or subcutaneous administration include aqueous and non-aqueous injection solutions. Formulations for injection may be in unit dosage forms, for example ampules or in multidosage forms. The formulation may be provided in a dry form that is to be reconstituted by adding water or other liquid before use. The formulation can be for administration topically, systemically or locally. The formulation can also be provided as an aerosol.

The formulations may contain nuclease inhibitors, antioxidants, buffers, antibiotics, salts, solutes that renders the formulation isotonic, lipids, carriers, diluents emulsifiers, chelating agents, excipients, fillers, drying agents, antioxidants, binding agents, solubilizers, stabilizers, antimicrobial agents, preservatives and the like.

In general, methods of administration of nucleic acids are well known in the art. The polynucleotide may be administered to the subject in any suitable manner. Nucleic acids can be administered by a number of routes including but not limited to oral, intravenous, intratumour, intraperitoneal, intramuscular, transdermal, subcutaneous, topical, sublingual, or rectal means. Suitable modes of administration include injection or infusion. Intravenous administration is a preferred mode of administration. In one embodiment the polynucleotide is administered by injection into a tumour of the subject.

Preferably an effective amount of the polynucleotide is administered to the subject. An effective amount is an amount that is able to treat one or more symptoms of a disease, halt or reverse the progression of a disease. The subject may be a subject in need of treatment. The subject is preferably a human.

Administration may be carried out at a single time point or repeatedly over a time period or from an implanted slow-release matrix. Other delivery systems include bolus injections, time-release, delayed release, sustained release or controlled release systems. Dosage and administration regimens may be determined by methods known in the art, for example with testing in appropriate in vitro or in vivo models, such as animal models to analyse efficacy, pharmacokinetics, pharmacodynamics, excretion, tissue uptake and the like by methods known in the art. A suitable way of finding a suitable dose is starting with a low amount and gradually increasing the amount. Dosing amounts used for the approved drugs mipomersen and fomivirsen can serve as guidance.

Preferably the disease being treated is cancer. Preferably the cancer being treated is one selected from the group consisting of kidney cancer (for example kidney renal papillary carcinoma or kidney clear cancer carcinoma), liver cancer (for example liver hepatocellular carcinoma), lung cancer (for example lung adenocarcinoma or lung squamous carcinoma), prostate cancer (for example prostate adenocarcinoma), or endometrial cancer (for example uterine corpus endometrial carcinoma), breast cancer, neuroblastoma or cervical cancer.

In one embodiment the cancer being treated is a drug resistant cancer, in particular a chemotherapy-resistant cancer, for example a cancer resistant to any of the known types of chemotherapy agents, such as, but not limited to actinomycin, all-trans retinoic acid, azacitidine, azathioprine, bleomycin, bortezomib, capecitabine, cisplatin, carboplatin, chlorambucil cyclophosphamide, cytarabine, daunorubicin, dicycloplatin, docetaxel, doxifluridine, doxorubicin, epirubicin, epothilone, etoposide, fluorouracil, gemcitabine, hydroxyurea, idarubicin, imatinib, irinotecan, lipoplatin, mechlorethamine, mercaptopurine, methotrexate, mitoxantrone, nedaplatin, oxaliplatin, paclitaxel, pemetrexed, picoplatin, satraplatin, teniposide, tioguanine, topotecan, valrubicin, vemurafenib, vinblastine, vincristine, vindesine and vinorelbine, and similar compounds. In particular the chemotherapy-resistant cancer is a cancer that is resistant against a platinum-based or platinum-containing chemotherapeutic substance, in particular a cancer that is resistant against a drug selected from the group consisting of cisplatin, carboplatin, dicycloplatin, lipoplatin nedaplatin, oxaliplatin, picoplatin, and satraplatin. In particular, the cancer being treated is a cancer that is resistant against cisplatin treatment.

A drug resistant cancer is typically a cancer in a patient where the patient does not respond to treatment based on clinical evaluation, for example where the tumour burden of the patient increases despite treatment. This is often referred to as that a patient "fails" treatment. However, in some embodiments, drug resistance may also be predicted by testing the genotype of the tumour.

Research Tool

The polynucleotide may also be used as a research tool. By using the polynucleotide, the role of SCAT7 may be investigated. For example, the role of SCAT7 may be investigated through administration of the polynucleotide to cells in culture or to animals. The polynucleotide may be administered to cells or animals as described herein. Alternatively, transgenic animals or cells that produce the inhibitory polynucleotides may be generated. For example, transgenic mice may be generated by methods known in the art. Cell lines stably expressing the polynucleotides may be generated. Any suitable phenotype or characteristic may be investigated. In particular, the role of SCAT7 in cancer may be investigated. This may be done by studying cell proliferation, senescence, migration invasion, metabolism, drug sensitivity or morphology. By using animal models, for example tumour growth, tumour invasion, metastasis, drug sensitivity or treatment, may be investigated.

Diagnosis

A high level of SCAT7 transcript correlates with poor prognosis in cancer patients. The level of SCAT7 can be determined in a patient in order to determine the prognosis of a patient. This can be used for making clinical decisions, choice of treatment (or no treatment) etc.

The level of SCAT7 transcript can be determined in a sample from a patient, preferably a sample from a tumour. The sample may be a tissue sample, for example taken after surgical removal of a tumour or by needle biopsy. The sample may also be a blood sample containing circulating tumour cells (CTCs), ascites fluid, blood, plasma, or similar. The sample may be a sample isolated from the patient. The method may involve determining the amount of SCAT7 in the sample.

In one embodiment the SCAT7-L (SEQ ID NO 1) transcript is detected and SCAT7-S is not detected. In one embodiment both sequences are detected simultaneously. This is preferably done by detecting the sequence that is common for SCAT7-L and SCAT7-S, i.e. SEQ ID NO 3.

The level of SCAT7 can be determined by methods known in the art such as RT-qPCR, northern blot, in situ hybridization, hybridization microarrays, RNA-seq etc. It is referred to Ausubel F M et al, Current Protocols in Molecular Biology (Wiley) for details. For example, the skilled person known how to design primers for quantitative PCR. RNA-seq uses a NGS approach to expression analysis.

Examples of probes that can be used for detecting the transcript in for example northern blot procedures include SEQ ID NO 4, 5, 8, 10, 12. Examples of suitable target sequences include SEQ ID NO 14-20.

The level of SCAT7 in a tumour sample can be compared to a sample from healthy tissue or to a normal value for healthy tissue. The level of SCAT7 can also be used to predict response to treatment involving inhibiting SCAT7, for example treatment as described herein.

Preferably the cancer being diagnosed is one selected from the group consisting of kidney cancer (for example kidney renal papillary carcinoma), liver cancer (for example liver hepatocellular carcinoma), lung cancer (for example lung adenocarcinoma or lung squamous carcinoma), prostate cancer (for example prostate adenocarcinoma), or endometrial cancer (for example uterine corpus endometrial carcinoma). In a preferred embodiment the cancer is kidney cancer or liver cancer.

EXAMPLES

Material and Methods

Cell Lines, Knockdown of Target Genes and Cloning

The adherent Caki-2, 786-O and HepG2 cell lines were purchased from CLS-GmbH (Germany). The lung adenocarcinoma (LUAD) cell lines A549 and H2228 were kindly provided by Bengt Hallberg's lab at the department of Medical Biochemistry and Cell Biology, University of Gothenburg. HeLa and MCF-7 cell lines were routinely maintained in our lab. The immortalized human fibroblasts cell lines, BJ-BRAF and TiG3-BRAF, were kindly provided by Andres Lund's lab (Biotech Research and Innovation Center, University of Copenhagen). We cultured Caki-2, 786-O and H2228 cell lines in RPMI 1640 medium (Gibco, Life Technologies, USA). A549, BJ-BRAF, TiG3-BRAF and MCF-7 cell lines were maintained in DMEM medium (Gibco, Life Technologies; USA). HeLa and HepG2 cell lines were maintained in MEM medium (Gibco, Life Technologies; USA). All media were supplemented with 2 mM L-glutamine, 1×Penicillin-Streptomycin antibiotic and 10% fetal bovine serum. All cell lines were tested negative for Mycoplasma contamination.

We performed transient transfection using siRNA and LNA molecules. Scramble siRNA and custom-designed siRNAs were synthesized by Sigma-Aldrich. We obtained both in vivo and in vitro grade negative control and custom-made LNA molecules from Exiqon. Transfection was carried out in the standard 24-well plates using Lipofectamin® RNAiMAX transfection reagent (Invitrogen, Calif.) according to the manufacturer's instructions with a final concentration of 35 pmol/well and 20 pmol/well of siRNA and LNA, respectively. The transfections were performed in three biological replicates and the efficiency of knock-down was confirmed by RT-qPCR.

We generated stable cell lines using Lentifect™ Purified shRNA lentivirus particles designed to target SCAT7 or scrambled negative control. The transduction efficiency was visualized by the integrated GFP reporter gene. The stable 786-O, Caki-2 and A549 knock-down cells were selected using 2 µg/ml, 3 µg/ml and 2 µg/ml of puromycin, respectively.

All siRNAs, LNAs and shRNA viral particles were designed to target SCAT7 exon (exon 2) that has no overlap with the protein-coding transcripts encoded from neighboring genes.

For SCAT7-L overexpression, SCAT7 full length transcript-coding DNA was cloned into pGEM-T Easy vector and the correct orientation was verified by sequencing. The confirmed clone was digested using NotI and HindIII enzymes and sub-cloned into the mammalian overexpression vector pcDNA3.1. HeLa, Caki-2 and A549 cells were transfected with either 1 µg of pcDNA3.1-SCAT7 vector or pcDNA3.1 empty vector using Lipofectamin® 2000 transfection reagent. The RNA levels were measured with RT-qPCR.

Polynucleotides Used for Knock-Down
The following polynucleotides were used in the examples.
a) Antisense DNA/GapmeRs

| Sequence name | sequence | SEQ ID NO | Target sequence | SEQ ID NO |
|---|---|---|---|---|
| LNA 1 | CAGTGCAC GCTTAGAA | 4 | TTCTAAGC GTGCACTG | 14 (under-lined) |
| LNA 2 | GTGCACGC TTAGAATA | 5 | TATTCTAA GCGTGCAC | 15 (bold) |

These polynucleotides were administered as single-strand DNA. The single-strand DNA hybridizes with SCAT7 and causes recruitment of RNAse H, resulting in breakdown of SCAT7. There are methylene bridges between the 2' oxygen and the 4' carbon of the nucleotides in positions 1, 2, 3, 14, 15, 16. LNA1 binds as indicated with underlined sequence, and LNA 2 binds as indicated with bold sequence, below (The two target sequences overlap partially).

>ENST00000419190.1 (SCAT7-L, SEQ ID NO 1)
cacggggcactggcctgggcaggtggcgggaacgttgctggggtgggc atctgtgctttcggctgccctctggcccaggaaattcctcccagggggc caggccagagatgggccaggcaggggggagggcaagtgagggaacatga -continued
acccctggctgacctgagtcagaaagctgctggcccctaaattccaga gattcagcaacaaagaggcctagtagggagaggagttactaggtttag gggttttttcccagaacacccaggactctggccaggggctggaaggtgc tccaggctcaatgctgggcaatactcatggattaattggtgctggctg ggcctgccagcctagtcgtggccccagggtccccactaaagggctcct tctccagcgcccactctgttggcaaggtcttcactaccatcacctgcc tggactccatccaagcatcagggttgctgcagtcgctcctgaagagac ccggctctgcttgaaagttcttccctcagcgcctgctggagccctccc tgccggagttgccagaatccacacggaatccacagatctgccctgatg atcatgaaggaatgcgaaagagcctggtaaaacgatatggacttgtgc aaatgcaaagcaatggtgaagtcatcacgaaccgcacagactggacag aactcctatctggctgcaatggcttgggttcagtcagcccaggggcca gagaattggctacaaagagctctggagtgcccctcctccaaataaag

TAttctaagcgtgcactgat

>ENST00000415582.1 (SCAT7-S, SEQ ID NO 2)
aagagatcagaattcagcttccccagggacagcaaggccaagaaggtg tccagatcctggcctctctccagatcttggactctctcaaggccaaga ctctctctcttaagatctctatctcaaggccaagatctctctccagat attggcctctctcaaggtacttccaagatctcagagggccattcactg tggatctaatatgaagacagagaaaccagccttccagaggagcggaca catttccttagtcccaggatacactttgtgtggaatccacagatctgc cctgatgatcatgaaggaatgcgaaagagcctggtaaaacgatatgga cttgtgcaaatgcaaagcaatggtgaagtcatcacgaaccgcacagac tggacagaactcctatctggctgcaatggcttgggttcagtcagccca ggggccagagaattggctacaaagagctctggagtgcccctcctcca aataaagTAttctaagcgtg

It should be noted that SEQ ID NO 4 and 5 can be used as regular DNA polynucleotides also, without being gapmers.

b) Short Hairpin Loops (shRNA)

| Seq name | Sequence | SEQ ID NO | Target sequence | SEQ ID NO |
|---|---|---|---|---|
| SCAT7-sh1 | gauccgGAUCUGCCCUGAU GAUCAUGAucaagagUCAU GAUCAUCAGGGCAGAUC uuuug | 6 | GATCTGCCCTGA TGATCATGA | 16 |
| SCAT7-sh2 | gauccgGAUAUGGACUUGU GCAAAUGCucaagagGCAU UUGCACAAGUCCAUAUC uuuuuug | 7 | GATATGGACTTG TGCAAATGC | 17 |

The plasmid pLKO.1-TRC was used for obtaining the sequence for short hairpins, by cloning in the target sequence and its reverse complimentary sequence into the vector. SEQ ID NO 6 and 7 shows the sequences of the resulting shRNA. The lowercase letters indicate parts contributed by the vector (pLKO.1-TRC). The sequence "ucaagag" is the "hairpin" structure sequence. Underlined sequence shows the sequence corresponding to the target sequence.

The DNA encoding the shRNA was cloned into a virus vector, which was used to transfect the cells. The plasmid was purchased from Sigma Aldrich in the form of packaged active lentiviral particles. Prior to the transduction, 50000 cells were seeded overnight. Then, the cells were infected with the viral particles in a ratio of 5 viral particles per cell. After incubating the cells with the viral particles for 16 hours, the viral particles were removed, and cell selected for 48 hours using puromycin.

The used target sequences for shRNA in SEQ ID NO 1 and SEQ ID NO 2 are underlined below:

>ENST00000419190.1 (SCAT7-L, SEQ ID NO 1)
cacggggcactggcctgggcaggtggcgggaacgttgctggggtgggc atctgtgctttcggctgccctctggcccaggaaattcctcccaggggc caggccagagatgggccaggcaggggagggcaagtgagggaacatga acccctggctgacctgagtcagaaagctgctggcccctaaattccaga gattcagcaacaaagaggcctagtagggagaggagttactaggtttag gggttttttcccagaacacccaggactctggccaggggctggaaggtgc tccaggctcaatgctgggcaatactcatggattaattggtgctggctg ggcctgccagcctagtcgtggccccagggtccccactaaagggctcct tctccagcgcccactctgttggcaaggtcttcactaccatcacctgcc tggactccatccaagcatcagggttgctgcagtcgctcctgaagagac ccggctctgcttgaaagttcttccctcagcgcctgctggagccctccc tgccggagttgccagaatccacacggaatccaca<u>gatctgccctgatg</u>

<u>atcatgaaggaatgcgaaagagcctggtaaaac</u>gatatggacttgtgc aaatgcaaagcaatggtgaagtcatcacgaaccgcacagactggacag aactcctatctggctgcaatggcttgggttcagtcagcccaggggcca gagaattggctacaaagagctctggagtgcccctcctccaaataaag tattctaagcgtgcactgat >ENST00000415582.1 (SCAT7-S, SEQ ID NO 2)
aagagatcagaattcagcttccccagggacagcaaggccaagaaggtg tccagatcctggcctctctccagatcttggactctctcaaggccaaga ctctctctcttaagatctctatctcaaggccaagatctctctccagat attggcctctctcaaggtacttccaagatctcagagggccattcactg tggatctaatatgaagacagagaaaccagccttccagaggagcggaca catttccttagtcccaggatacactttgtgtggaatccaca<u>gatctgc</u>

<u>cctgatgatcatgaaggaatgcgaaagagcctggtaaaacgatatgga</u>

<u>cttgtgcaaatgc</u>aaagcaatggtgaagtcatcacgaaccgcacagac tggacagaactcctatctggctgcaatggcttgggttcagtcagccca ggggccagagaattggctacaaagagctctggagtgcccctcctcca aataaagtattctaagcgtg c) siRNA The following siRNA were used, where SEQ ID 8 and 9 hybridizes, SEQ ID NO 10 and 11 hybridizes and SEQ ID NO 12 and 13 hybridizes. The siRNA were designed with 3'TT (deoxynucleotides) overhang.

| Sequence name | Orientation | Design sequence | SEQ ID NO | Target sequence | SEQ ID NO |
|---|---|---|---|---|---|
| siRNA1 | s | CACAGACUGGA CAGAACUCUU | 8 | GAGTTCTGTC CAGTCTGTG | 18 |
| siRNA1 | a | GAGUUCUGUCC AGUCUGUGUU | 9 | | |
| siRNA2 | s | GCCAGAGAAUU GGCUACAAUU | 10 | GCCAGAGAAT TGGCTACAA | 19 |
| siRNA2 | a | UUGUAGCCAAU UCUCUGGCUU | 11 | | |
| siRNA3 | s | CCCUGAUGAUC AUGAAGGAUU | 12 | CCCTGATGAT CATGAAGGA | 20 |
| siRNA3 | a | UCCUUCAUGAU CAUCAGGGUU | 13 | | |

The used target sequences for the siRNA were shown underlined below.

>ENST00000419190.1 (SCAT7-L, SEQ ID NO 1)
cacggggcactggcctgggcaggtggcgggaacgttgctggggtgggc atctgtgctttcggctgccctctggcccaggaaattcctcccagggc caggccagagatgggccaggcaggggagggcaagtgagggaacatga acccctggctgacctgagtcagaaagctgctggcccctaaattccaga gattcagcaacaaagaggcctagtagggagaggagttactaggtttag gggtttttcccagaacacccaggactctggccaggggctggaaggtgc tccaggctcaatgctgggcaatactcatggattaattggtgctggctg ggcctgccagcctagtcgtggcccagggtccccactaaagggctcct tctccagcgccactctgttggcaaggtcttcactaccatcacctgcc tggactccatccaagcatcagggttgctgcagtcgctcctgaagagac ccggctctgcttgaaagttcttccctcagcgcctgctggagccctccc tgccggagttgccagaatccacacggaatccacagatct**gccctgatg
atcatgaaggaatgcgaaagagcctggtaaaacgatatggacttgtgc aaatgcaaagcaatggtgaagtcatcacgaaccgcacagactggacag
aactcctatctggctgcaatggcttgggttcagtcagcccaggggcca
gagaattggctacaa**agagctctggagtgcccctccctccaaataaag tattctaagcgtgcactgat >ENST00000415582.1 (SCAT7-S SEQ ID NO 2)
aagagatcagaattcagcttccccagggacagcaaggccaagaaggtg tccagatcctggcctctctccagatcttggactctctcaaggccaaga ctctctctcttaagatctctatctcaaggccaagatctctctccagat attggcctctctcaaggtacttccaagatctcagagggccattcactg tggatctaatatgaagacagagaaaccagccttccagaggagcggaca catttccttagtcccaggatacactttgtgtggaatccacagatctg**c
cctgatgatcatgaaggaatgcgaaagagcctggtaaaacgatatgga cttgtgcaaatgcaaagcaatggtgaagtcatcacgaaccgcacagac
tggacagaactcctatctggctgcaatggcttgggttcagtcagccca ggggccagagaattggctacaa**agagctctggagtgcccctccctcca aataaagtattctaagcgtg Flow Cytometry and Cell Cycle Profiling We assessed the cell cycle profiles of transient knock-down cells and control cells 48 h post-transfection. The media were aspirated and the cells were washed with PBS, trypsinized, pelleted by centrifugation, washed twice with cold PBS, fixed with ice-cold 70% ethanol and stored at −20° C. for at least 2 h. The fixed cells were re-collected by centrifugation, re-suspended in PBS and kept for 30 min at 37° C. Then, cells were collected and stained with PI solution containing 1% RNase A in PBS and kept at 4° C. for at least 4 h. The PI-stained cells were assayed using Eclipse single cell flow cytometry system ec800 and data were analyzed with the manufacturer's software. The cell cycle profiling was validated on another system using Nucleo-Counter NC-3000 platform (Chemometec, Denmark). The fixed cells were stained with DAPI solution provided by the manufacturer and analyzed according to manufacturer's instructions. All knock-down experiments were assayed three times independently and statistical significance was derived using two-sided unpaired Student's t-test.

Proliferation and Vitality Assays

We assayed the proliferation capacity of transiently transfected cells 48 h post-transfection using CellTiter 96® Non-Radioactive Proliferation Assay kit (Promega, USA) with some modifications to the manufacturer's protocol. The media were aspirated and cells were washed once with PBS, and 425 µl of fresh medium plus 75 µl of MTT dye were added and incubated at 37° C. in dark for 4 h. Then, each reaction was terminated using 500 µl of stop solution and the cells were kept overnight in dark at 4° C. to solubilize the MU dye. The dye intensity was measured using microplate reader at 570 nm. Standard deviation (SD) and statistical significance were derived from three independent experiments. For assaying the proliferation capacity of stable knock-down cell lines, we seeded the same number of control and knock-down cells and applied the same protocol used in the transient transfection experiments. We performed the vitality assay for transient knock-down cells and stable knock-down cell lines using NucleoCounter NC-3000 platform. The cells were harvested and stained with a mixture of VB-48™, PI and acridine orange dyes according to the manufacturer's instructions. The results were viewed and analyzed by the manufacturer's software. Each experiment was repeated at least three times and statistical significance was derived using two-sided unpaired Student's t-test.

Apoptosis and Senescence Assays

We performed apoptosis assay for transiently transfected cells 48 h post-silencing using Caspase-Glo® 3/7 Assay (Promega, USA) and measured the luminescence according to the manufacturer's instructions. For stable knock-down cells, in addition to the Caspase-Glo® 3/7 Assay, we performed fluorescent-based Guava Caspase 3/7 FAM Assay (Merk Millipore, Germany) following the manufacturer's instructions. We analyzed the caspase 3/7 FAM activity using NucleoCounter NC-3000 platform. For detection of senescence in fibroblasts and HeLa cells, we carried out transient transfections for 72 h. In case of A549 stable knock-down cells, we seeded the cells at less confluency for 72 h. We then detected the senescent cells using Senescence β-Galactosidase Staining Kit (Cell Signaling Technology, USA) following the manufacturer's instructions.

Soft Agar Colony Forming Assay

We used a standard procedure for soft agar colony forming assays in a 24-well plate. In each well, we plated 500 µl of 1:1 mix of 1% molecular biology grade agar and 2× medium (RMPI 1640 or DMEM) supplemented with 20% FBS, then agar layer was left to harden for 30 min. The soft agar layers were prepared by mixing either stable knock-down cells or control cells with a 500 µl mix of 1:1 0.6% agar and 2× medium supplemented with 20% FBS. The soft agar layers containing 2500 cells/well were left for 15 min to harden and then we added 500 µl of 1× RPMI 1640 or DMEM supplemented with 10% FBS on the top of the agar layers to prevent any possible dehydration. For each cell line, we plated 10 wells. After 10 days of incubation at 37 C, we captured pictures of each well using an automated Z-stack function of the EVOS FL Auto Cell Imaging System (ThermoFisher Scientific). We counted the number of total colonies in each condition and we measured the surface area of at least 20 representative colonies of each cell line. Statistical significance was derived using two-sided unpaired Student's t-test.

Cell Migration and Invasion Assays

We assayed the migration properties of stable knock-down cells using Oris™ Universal Cell Migration Assembly Kit (Platypus Technologies). Briefly, stable knock-down or control Caki-2, 786-O and A549 cells were seeded into a 96 well plate with Oris Cell Seeding Stoppers at $1.3 \times 10^4$, $1 \times 10^4$ and $1.7 \times 10^4$ cells per well, respectively. To create the detection area, the stoppers were removed after 16 hours; stoppers were left in place for the reference wells (t=0 pre-migration control) until the results are read. We used EVOS™ FL Auto Imaging System (Life Technologies) to detect cell migration at 8 h and 24 h post seeding in case of Caki-2 and 786-O cell lines, and 24 h and 48 h in the case of A549 cells. The area of pre-migration (t=0) and post-migration (t=8 h and 24 h) were calculated for each condition. All the experiments were performed in quadruplicates.

Transwell invasion assay was performed using the 24 well plates BD BioCoat Matrigel Invasion Chamber (BD Biosciences) with 8 µm inserts. For transiently transfected cells, we first performed siRNA and scramble sequence transfection, as described previously. Eight hours post-transfection $3.5 \times 10^4$ Caki-2 transfected cells were re-suspended in 1% FBS RPMI-1640 media and seeded into matrigel-coated inserts. For Caki-2 and A549 stable knock-down cell lines, $3 \times 10^4$ cells were re-suspended in the appropriate medium supplemented with 1% FBS and seeded into the inserts. Negative control cells were also seeded at the same confluence. Lower chambers were filled with 500 µL of complete medium with 10% FBS as a chemoattractant agent. Invasion chambers were incubated at humidified 5% $CO_2$ incubator at 37° C. for 22 hours. Non-migrated cells were scraped from the interior of the inserts by using a cotton-tipped swab. Cells on the lower surface of the membrane were fixed and stained using the Snabb-Diff kit (Labex), according to the manufacturer's instructions. After staining, the inserts were washed twice in distilled water, and then the membranes were removed from the inserts and kept in slides. Invading cells were photographed at 20× magnification, and the total number of migrated cells was counted using the EVOS™ FL Auto Imaging System (Life Technologies).

Developing Mouse Xenografts

Kidney renal cell cancer (KIRC) and Lung adenocarcinoma (LUAD) xenograft models were generated using stable knock-down cells. 786-O and A549 stable knock-down cells or control cells were re-suspended in cold PBS with 20% matrigel. We engrafted $1 \times 10^6$ cells subcutaneously in the right flank of six week old female Balb/C nude mice (Janvier labs). We used 8 mice per group in case of KIRC xenografts and 6 mice per group in LUAD xenografts. Eight weeks post-engrafting, we dissected and measured tumours volumes using the following formula: ((Long Side)×(Short side)$^2$)/2. For the treatment of established LUAD tumours with LNA, we engrafted $1 \times 10^6$ wild-type A549 cells subcutaneously. We began treatment with in vivo grade LNA molecules at a final concentration of 60 pmol when the outside volume of the majority of the tumours reached around 0.5 cm$^3$. We used 4 mice per group. The desired LNA concentration was diluted in phosphate saline buffer (PBS) to reach a final volume of 100 µl. The LNA molecules in PBS were injected subcutaneously to the adjacent vicinity of the developing tumours. The injections were done every three days for 12 days (4 injections in total). After terminating the experiment, we dissected the tumours and collected blood samples, livers, spleens and kidneys from all mice. The animal study protocol was reviewed and approved by the Animal Ethical Review Board, University of Gothenburg, Sweden (Ethical permit no. 45-2015).

Example 1—SCAT7 Modulates Hallmarks of Cancer Across Multiple Cell Lines

Analysis of expression analysis across the TCGA datasets indicated that a SCAT7 transcript (Ensembl: RP11-465N4.4, Genbank: ENST00000419190.1) comprising SEQ ID NO 3 is significantly upregulated in several cancers (BLCA, BRCA, KIRP, LIHC, LUAD, LUSC, PRAD and UCEC) (FIG. 1).

Example 2—Prognostic Value of SCAT7 in Kidney Cancer and Lung Cancer

To determine the clinical importance of the SCAT7 lncR-NAs, RNA-Sequencing data and clinical information from patients with 14 different cancers was obtained from TCGA (The Cancer Genome Atlas). The RNA-Seq of the patient samples were aligned with hg19 genome annotation using HISAT aligner. The RNA-seq mapped reads were subsequently quantified with the HTSeq computational tool. The reads were quantified to library size and gene length to generate RPKM (reads per kilobase of transcript per million mapped reads) for each RNA in the human transcriptome (more than 20 000 protein coding RNA and several thousands of long non-coding RNAs).

To obtain the clinical significance of SCAT7 lncRNA, a detailed analysis was done on the patients categorized into two groups based on SCAT7 RNA expression as high and low expression groups. Survival analysis was done using Kaplan-Meier estimator and log-rank test using the R-package survival. In our analysis, the high expression of SCAT7 is associated with poor survival showing that the SCAT7 lncRNA is involved in the aggressive nature of the cancer (FIG. 2a).

The main objective of determining new prognostic markers is whether it can be combined with existing clinical models. So we included the standard prognostic markers such as tumour stages, grades, size and age in the cox regression analysis along with SCAT7. We got a hazard ratio of 1.4 representing high expression of SCAT7 is 40% more hazardous compared to the low expression group (FIG. 2b).

Brier prediction curve were used to confirm the predictability of our multivariate model. The performance evaluation provided lower Brier score of the model compared to reference model indicating less prediction error. From overall analysis we identified SCAT7 can act as an independent prognostic marker.

Figure 2A:
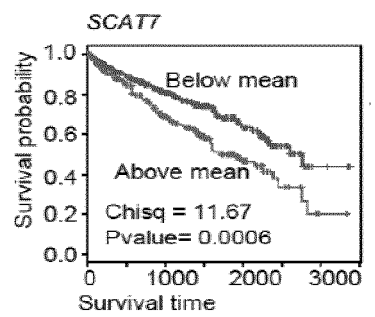
FIG. 2a is a Kaplan-Meier plot that shows overall survival difference in KIRC patients. The higher expression of SCAT7 is correlated with poor survival.
Figure 2B:
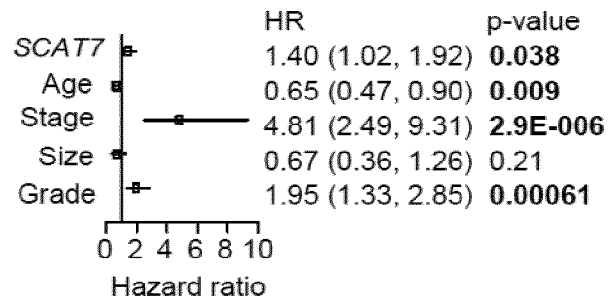
FIG. 2b Estimation of hazard ratio (HR) associated with SCAT7 expression and clinical co-variates using Cox regression model in KIRC patients.
Figures 2C, 2D, 2E, 2F:
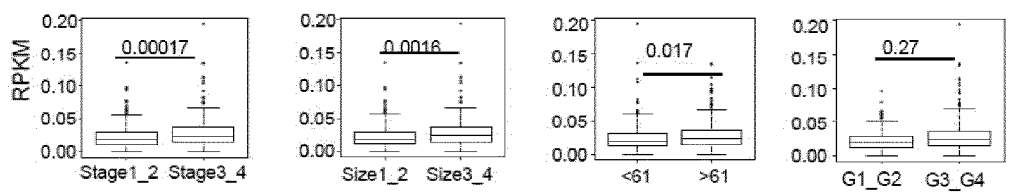
FIG. 2c Boxplot shows the median expression of SCAT7 in different pathologic stages. Higher expression is significantly associated with advanced stages (stage 3 and 4) in KIRC patients.
FIG. 2d Boxplot shows the median expression of SCAT7. Higher expression is significantly associated with elevated tumour size (size 3 and 4) in KIRC patients.
FIG. 2e Boxplot shows the median expression of SCAT7 in different age groups. Higher expression is significantly associated with higher age (more than 61 year-old) in KIRC patients.
FIG. 2f Boxplot shows the median expression of SCAT7 in different tumour grades. There is no significant difference in the expression between different groups.

Also our detailed clinical investigations demonstrated its potential to independently predict the clinical outcome in KIRC and colon adenocarcinoma patients (FIG. 2a).

Example 3—Role of SCAT7 for Cancer Cell Properties

Figure 3A:
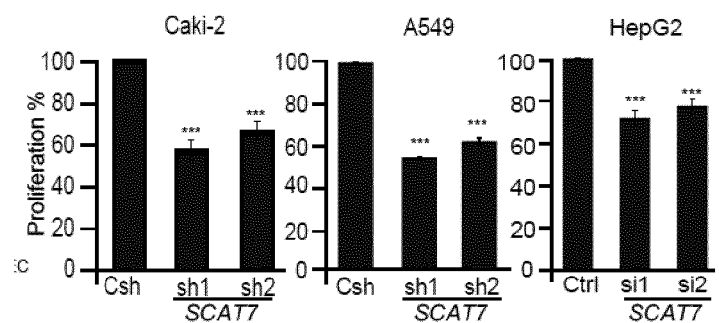
FIG. 3a shows proliferation capacity measured by MTT colorimetric assay of Caki-2, A549 and HepG2 cells upon silencing of SCAT7 with two different shRNAs or siRNAs.
Figure 3B:
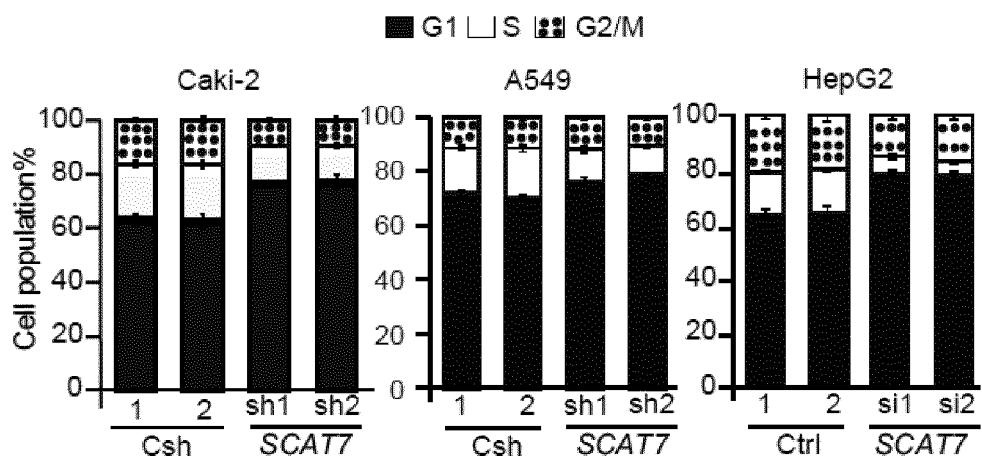
FIG. 3b show cell cycle profiles of Caki-2, A549 and HepG2 cells depleted with two different shRNAs or siRNAs targeting SCAT7. Inhibition of SCAT7 induces a significant accumulation at G1 phase with an inhibition of the S-phase.

Next the functional role of SCAT7 in the maintenance of cancer cell hallmarks in different cell lines representing multiple cancer types was investigated. To this end, SCAT7 was downregulated in cell lines representing KIRC (Caki-2 and 786-O), LUAD (A549 and H2228), LIHC (HEPG2) and BRCA (MCF7) using siRNA or short hairpin RNA (shRNA) Downregulation of SCAT7 in Caki-2 (2 shRNAs and 2 siRNAs), 786-O (1 shRNA and 2 siRNAs), A549 (2 shRNAs and 2 siRNAs), H2228 (2 siRNAs), HepG2 (2 siRNAs), and MCF7 (2 siRNAs) cells decreased cell proliferation (FIG. 3a), and affected cell cycle progression, with preferential accumulation of cells at G1/S phase (FIG. 3b) Notably, compared to other cell lines, the transient knock-down of SCAT7 in H2228 cells induced a significant accumulation of cells at G2/M phase. Since H2228 and HepG2 cell lines were sensitive to long term SCAT7 downregulation using shRNA particles, SCAT7 downregulation in these cell lines was performed using transient transfection of siRNA. Similarly, 786-O cell line was also sensitive to one of the shRNA particles. This indicates that SCAT7 is very important for cell homeostasis.

Figure 3C:
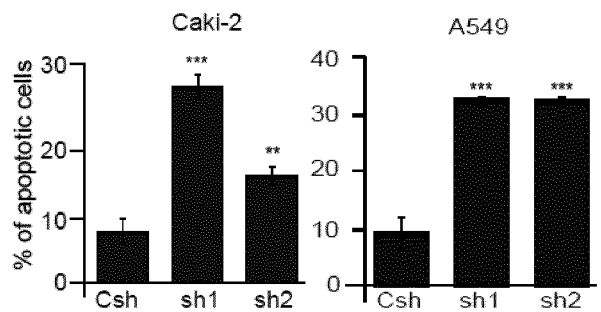
FIG. 3c shows analysis of apoptosis on stable SCAT7 knock-down Caki-2 and A549 cells, with a significant increase of caspase 3/7 activity in the silenced cells compared to the control cells. Data are expressed as percentage of apoptotic cells populations evaluated 48 h post-seeding the same number of knock-down and control cells.
Figure 3D:
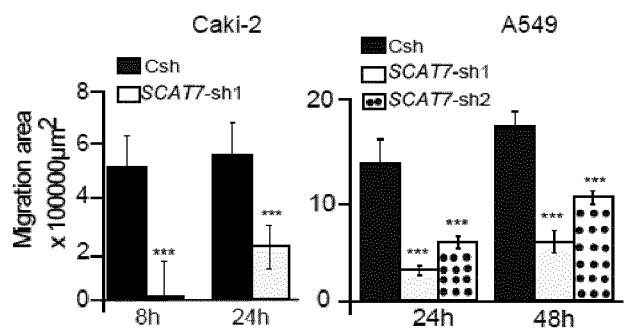
FIG. 3d shows results from migration assay of stable SCAT7 knock-down Caki-2 and A549 cells at different time points. Differential migration areas were calculated with respect to a starting time point (t=0) of each corresponding control. The stable SCAT7 knock-down cells show an impaired migration capacity compared to control cells.
Figure 3E:
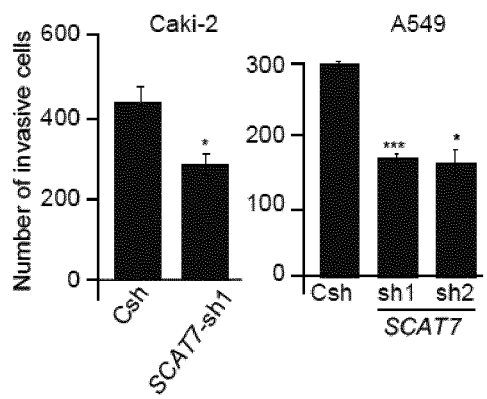
FIG. 3e shows results from matrigel transwell invasion assay in Caki-2 and A549 SCAT7 stable knock-down cells showing a significant reduction of invasive properties in the SCAT7 depleted cells. The number of invasive cells was counted 24 h post-seeding the same number of knock-down and control cells.
Figure 3F:
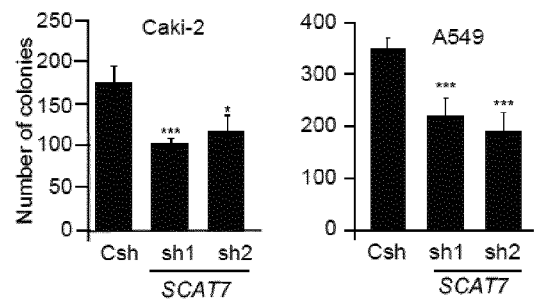
FIG. 3f shows results from soft agar colony forming assay analysis in Caki-2 and A549 knock-down cells. The average number of colonies is significantly reduced in knock-down cells compared to control cells.
Figure 3G:
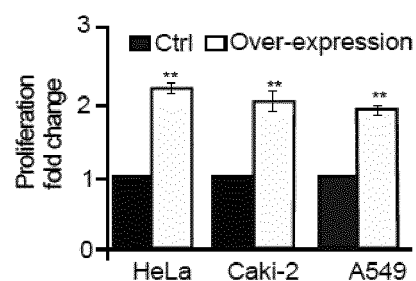
FIG. 3g shows results from MTT proliferation assay of HeLa, Caki-2 and A549 cells overexpressing SCAT7, which exhibit a significant increase of the proliferative capacity compared to the control cells.

We next focused our experiments on Caki-2, 786-O and A549 stable knock-down cell lines to elucidate the functional role of SCAT7 on other cancer hallmarks such as apoptosis, cell migration and invasion. Stable knockdown of SCAT7 in the Caki-2 and A549 cell lines increased caspase 3/7 activity (FIG. 3c) decreased migration and invasive capacity compared to the control cells (FIGS. 3e and 3) The invasion capacity was severely suppressed in the Caki-2 and A549 stable knock-down cells, while the effect was very limited in the case of 786-O stable knock-down cells. Additionally, we investigated the anchorage-independent cell growth using soft agar colony formation assay for Caki-2, 786-O and A549 stable knock-down cell lines 10 days after incubation (FIG. 3f)). In comparison to the control cells, the ability of all stable knock-down cells to form anchorage-independent colonies was drastically reduced. The total number of colonies, as well as the area of each individual colony was significantly decreased. In accordance with its role in restricting the cellular proliferation capacity upon knockdown, overexpression of SCAT7 significantly increased cell proliferation by 2.25 fold, 2.08 fold and 1.9 fold in HeLa, Caki-2 and A549 cells, respectively (FIG. 3g). Collectively, our data demonstrate the critical role of SCAT7 in regulating some of the most important cancer hallmarks in multiple cancer cell lines.

Example 4—Downregulation of SCAT7 Induces Cell Senescence

Figure 3H:
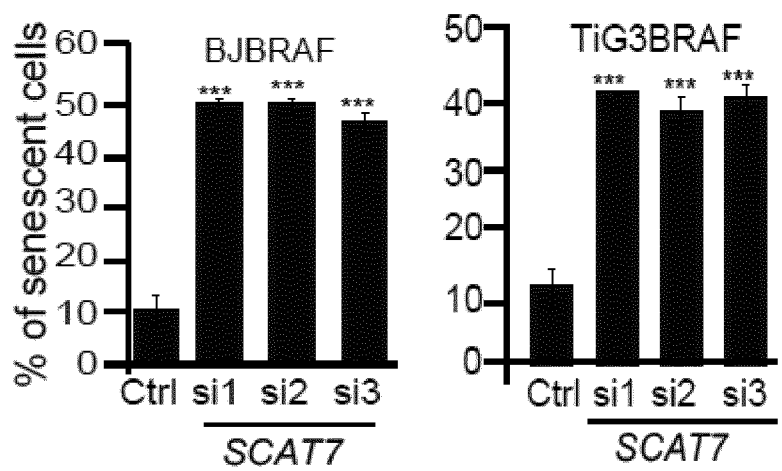
FIG. 3h shows results from colorimetric β-galactosidase staining of BJ-BRAF and TiG3-BRAF human fibroblast cell lines 72 h post-silencing of SCAT7 using three different siRNAs.
Figure 3I:
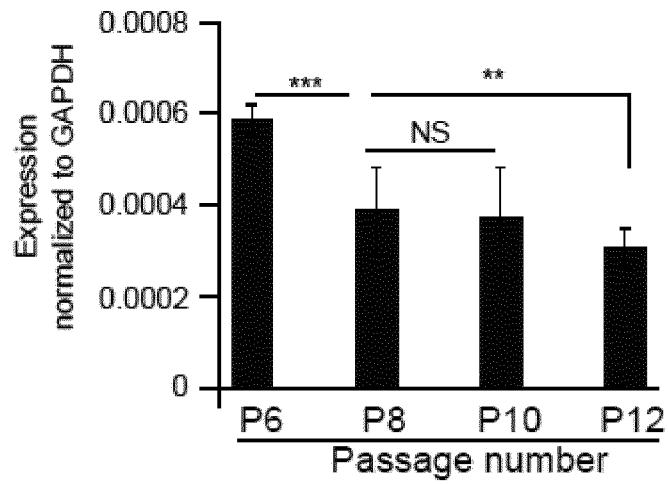
FIG. 3i shows real-time qPCR quantification showing a spontaneous decline in SCAT7 expression levels in serial passages of BJ-BRAF cells. NS indicates insignificant changes.
Figure 3J:
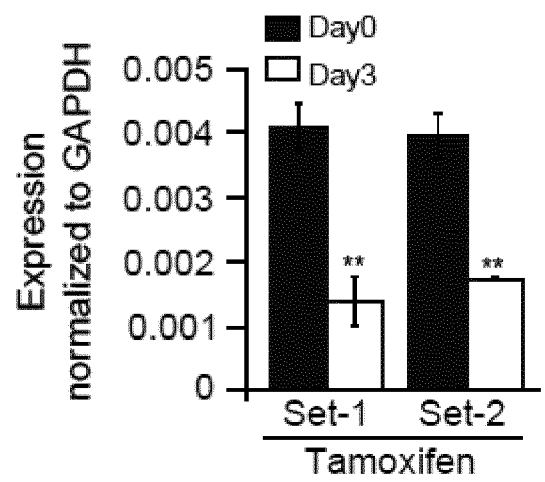
FIG. 3j Expression levels of SCAT7 in BJ-BRAF cells at day 0 and day 3 upon senescence induction using 200 nM of tamoxifen. The data represent two independent experiments performed at one passage interval indicating the significant reduction in SCAT7 expression in response to senescence induction.
Figure 3K:
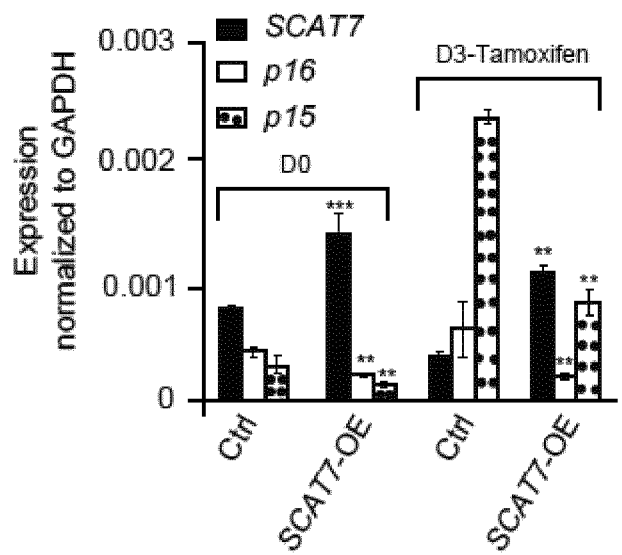
FIGS. 3kl and 3l show quantified expression levels of SCAT7, p16, p15 and IL8 in control BJ-BRAF and SCAT7-overexpressing cells at day 0 and three days post-treatment with tamoxifen. In comparison to the respective time point, overexpression of SCAT7 leads to a significant reduction in expression levels of p16, p15 and IL8.
Figure 3L:
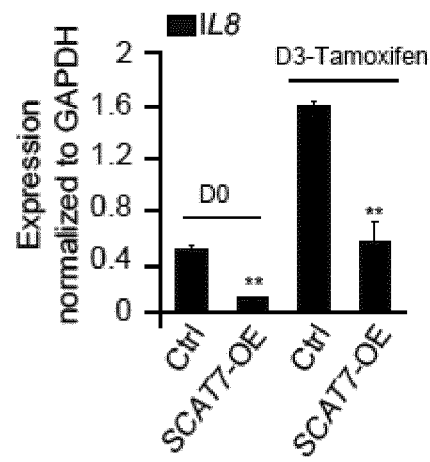
FIG. 3m show quantification of senescent cells upon SCAT7 KD in A549 cells. The values are expressed as a percentage of the whole cells populations.
Figure 3M:
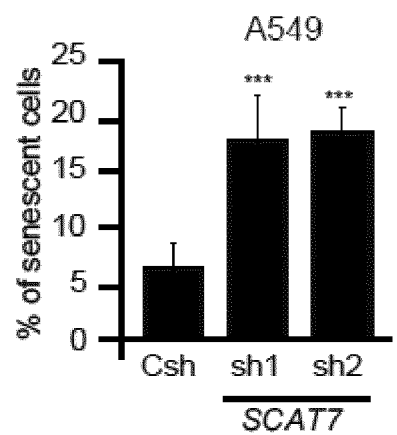

Cell senescence, induced in response to increased oncogenic signalling, is closely connected to cell cycle progression and cell proliferation (Montes and Lund, 2016; Serrano et al., 1997). Given that SCAT7 induces cell cycle perturbations with significant inhibition of the S-phase and deformed cell morphology (data not shown), the contribution of SCAT7 to cell senescence was investigated. To this end two fibroblast cell lines; BJ and TiG3 immortalized with BRAF transformation were used (Montes et al., 2015) Transient downregulation of SCAT7 using three different iRNAs for 72 hours induced senescence in both the cell lines as indicated by β-galactosidase staining and significant upregulation of senescence marker genes such as p16, IL8 and p21 (FIGS. 3h and 3k 3l). We have also observed a spontaneous decrease in the expression levels of SCAT7 during serial passaging of the fibroblast cells maintained under normal culturing conditions (FIG. 3i). Importantly, the cells overexpressing SCAT7 were able to bypass tamoxifen-induced senescence as indicated by less β-galactosidase activity and transcriptional repression of the key senescence marker genes p16, p15 and IL8 (FIGS. 3j, 3k, 3l 3m). Taken together, our data demonstrate that SCAT7 plays a crucial role in regulating cellular senescence in multiple cell lines; indicating cross-talk between cell proliferation, cell cycle progression and senescence.

Example 5—Role of SCAT7 in Cell Signalling

Figure 4:
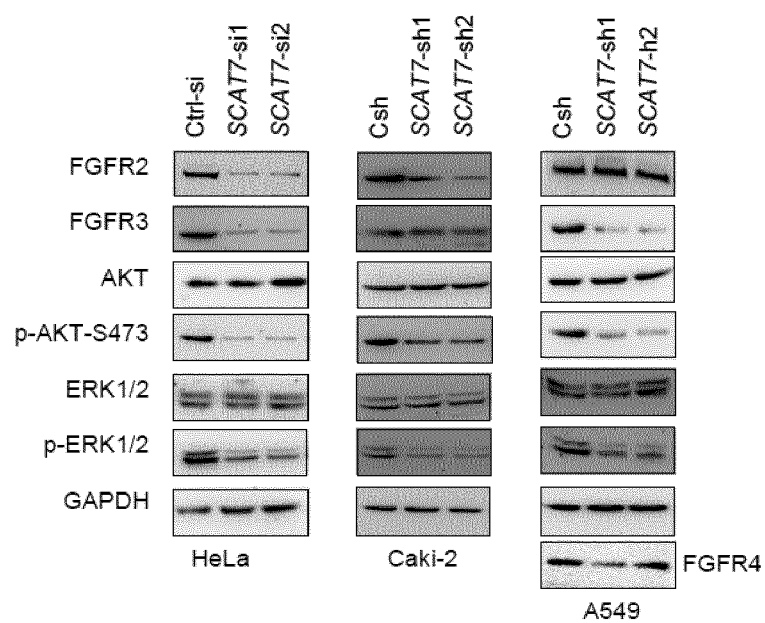
FIG. 4 shows western blots for the identification of the proteins levels of FGFR2, FGFR3, AKT, phospho-AKT, ERK1/2 and phospho-ERK1/2 upon silencing of SCAT7 in HeLa, Caki-2 and A549 cell lines.

In order to gain an insight into the SCAT7 mediated molecular pathways and cancer-related processes, high-throughput RNA sequencing of HeLa, Caki-2 and A549 cells upon SCAT7 downregulation was performed. Subsequent functional enrichment analysis of the RNA-seq data for molecular pathways revealed that the depletion of SCAT7 affected major signalling pathways and vital biological processes. For instance, among the molecular pathways, FGF/FGFR and the downstream PI3K/AKT and Ras/MAPK pathways were largely affected while cell proliferation, cell adhesion, cellular senescence, cell migration and apoptotic processes were the most perturbed biological processes. To reinforce the functional role of SCAT7 in the affected signalling pathways, we validated some of the dysregulated genes at transcriptional and translation levels (FIG. 4) in the SCAT7 knockdown cells; including FGFR members, Phospho-Ser473 AKT (p-AKT) and Phospho-Thr202/Tyr204 ERK1/2 (p-ERK1/2). We detected significant reduction in the FGFR, p-AKT and p-ERK1/2 levels in the SCAT7 knockdown HeLa, Caki-2 and A549 cells.

Example 6—SCAT7 is a Therapeutic Target in the Treatment of Cancers

Figure 5A:
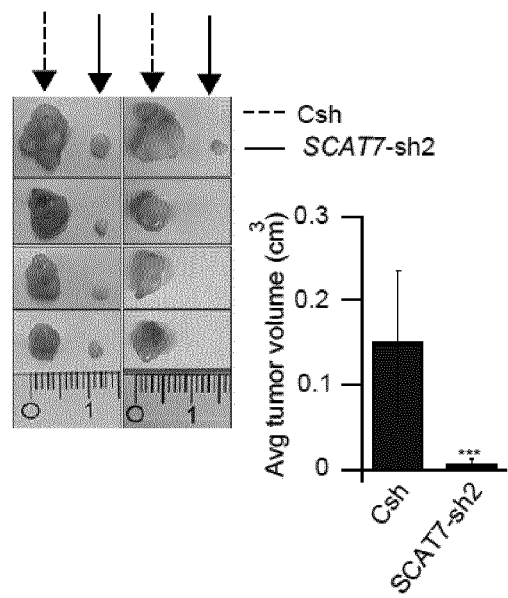
FIG. 5a shows tumour growth in Balb/c nude mice eight weeks after subcutaneous inoculation of $1 \times 10^6$ 786-O cells, control-sh or SCAT7-sh2 (n=8 each group). Tumour volumes ($cm^3$) are expressed as mean±SD, compared to control sh.
Figure 5B:
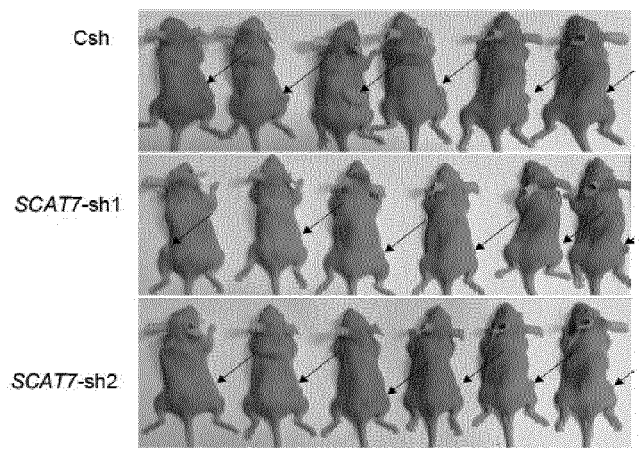
FIGS. 5b, c shows tumours from Balb/nude mice eight weeks after subcutaneous injection of $1 \times 10^6$ A549 cells, treated with control sh, SCAT7-sh1, and SCAT7-sh2, respectively, (n=6 for each group). Tumour volumes are expressed as mean±SD, compared with control shRNA.
Figure 5C:
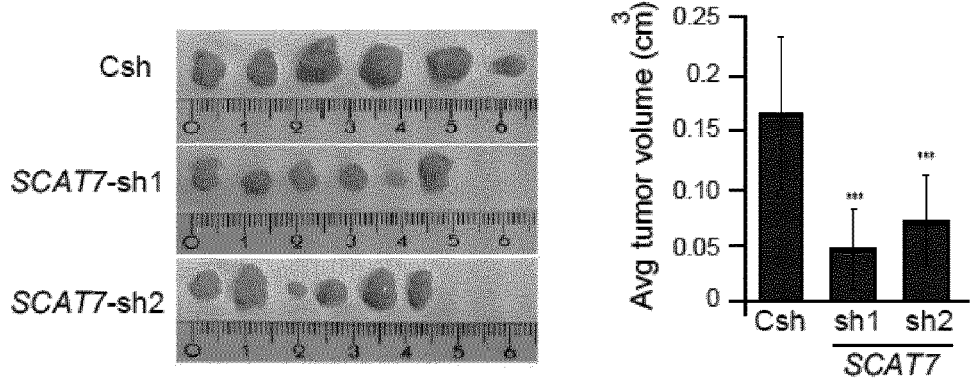
FIG. 5d are immunohistochemistry images of Ki67 staining in xenografts generated from subcutaneous transplantation of A549 cells stably expressing control sh, SCAT7-sh1, or SCAT7-sh2 into nude mice showing higher proliferation rate in control sh cells compared to the SCAT7 knock-down cells.
FIG. 5e shows tumour Growth Inhibition (TGI) for A549 subcutaneous Balb/c nude xenografts treated with 60 pmol of SCAT7 anti-sense oligonucleotides, LNA-1 and LNA-2, respectively, for a total of four injections.
FIG. 5f shows real-time qPCR validation of the relative expression of SCAT7 in A549 tumours collected after treatment with control LNA, LNA-1 and LNA-2, showing a significant downregulation of SCAT7 in the tumours treated with the LNAs compared to the negative control. Values are normalized to endogenous GAPDH.
FIG. 5g shows gene expression of SCAT7 targets in A549 tumours treated with negative Control, LNA-1, and LNA-2. Values are expressed as fold change normalized to endogenous GAPDH.
Figure 5D:
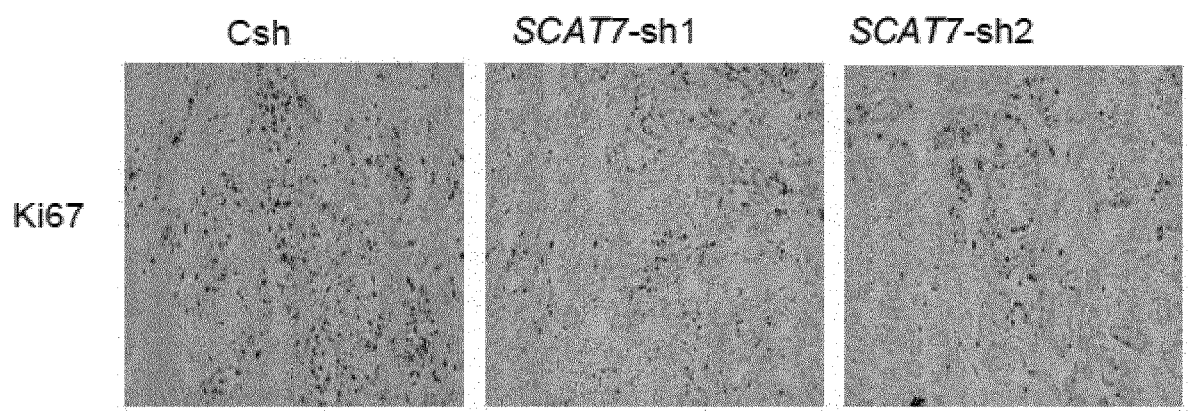

The above in vitro data as well as the mechanistic studies clearly demonstrate the oncogenic nature of SCAT7 and its crucial role in promoting cancer-associated signalling pathways. Therefore the role of SCAT7 in malignant tumourigenesis in vivo was investigated. Towards this, we generated two different xenograft models using female BALB/c nude mice engrafted with either 786-O or A549 SCAT7 stable knockdown cells expressing sh1 or sh2 short hairpin RNA. Eight weeks post engrafting, both 786-O (FIG. 5a) and A549 (FIGS. 5b and 5c)) SCAT7 knockdown cells failed to develop tumours and showed a significant decrease in growth parameters compared to the control cells expressing scrambled shRNA sequence. Histological examination and Ki67 immunohistochemistry staining of the dissected tumours confirmed the restricted proliferation capacity of SCAT7 knockdown cells in vivo (FIG. 5d).

Figure 5E:
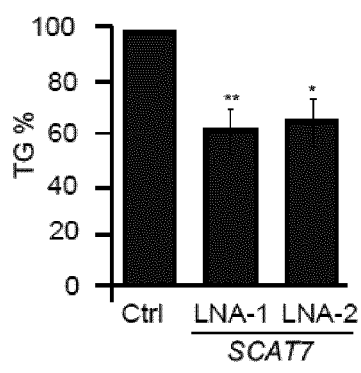
Figure 5F:
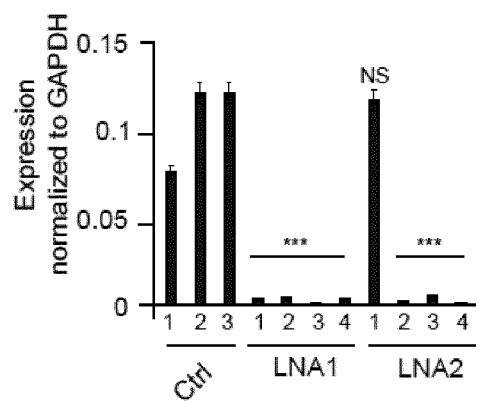
Figure 5G:
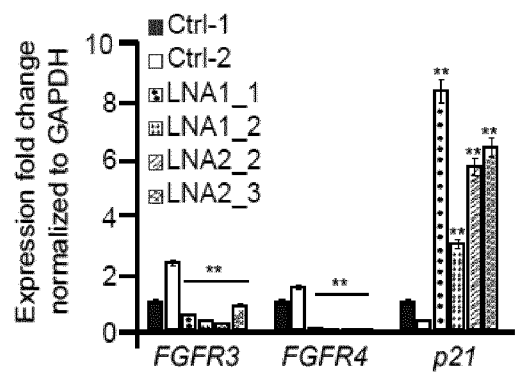

Next the hypothesis that SCAT7 can serve as a target for therapeutic intervention was tested. Wild-type A549 cells were engrafted into female BALB/c nude mice and were allowed to develop subcutaneous tumours. Six weeks post-engrafting, two independent LNA anti-sense oligonucleotides targeting SCAT7 we subcutaneously injected, twice a week, (see Experimental Procedures). We measured the tumour volumes after a course of four injections and we observed 40% tumour growth inhibition (TGI) in SCAT7 LNA groups in comparison to the scrambled LNA control group (FIG. 5e). We have also monitored the weight of the mice during the tumour development and post-injections to score for any weight loss induced by the LNA treatment. Adding to that, we measured the weights and sizes of liver, spleen and kidneys to assess the cytotoxicity of the treatment (data not shown). Importantly, we didn't find any significant difference in cytotoxicity between the different groups. Moreover, following tumour dissection, we lysed the tissues and extracted RNA from all tissues to confirm the knockdown efficiency of SCAT7 in vivo (FIG. 5f). Interestingly, a significant reduction in tumour growth was observed only when there was downregulation of SCAT7 but not in tumours where SCAT7 levels were not affected. Then, we checked the expression levels of different SCAT7 target genes in vivo, including FGFR3, FGFR4 and p21 (FIG. 5g). Coming in line with the in vitro data, FGFR3 and FGFR4 were significantly downregulated while p21 was highly upregulated in tumours treated with SCAT7 LNAs. Ki67 staining of the dissected tumours revealed the potent effect of SCAT7 targeting on cancer malignancy in vivo. Likewise, SCAT7 silencing promoted a higher frequency of apoptotic events, as determined by TUNEL staining, compared to the controls indicating the efficacy of our treatment strategy.

Example 7—Treatment of Patient Derived Xenograft Tumours

Figure 6A:
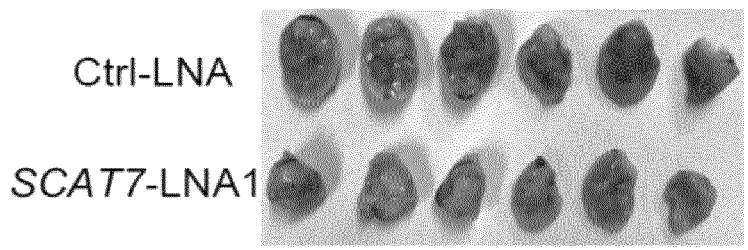
FIG. 6a shows lung PDX tumours extracted after a course of five LNA injections using scrambled sequence or SCAT7 LNA.
Figure 6B:
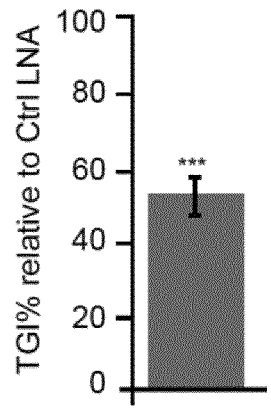
FIG. 6b shows tumour growth inhibition percentage (TGI) showing 46% inhibition of the tumour volumes upon SCAT7 LNA injection relative to the scrambled LNA control.
Figure 6C:
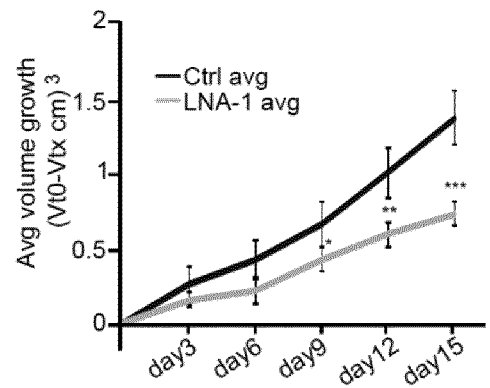
FIG. 6c shows average volume growth of PDX tumours was calculated by subtracting the average volume at a given time point following the LNA injection from the initial average volume.

SCAT7 LNA intervention was implemented in patient-derived xenograft using a lung metastatic patient-derived xenograft (PDX) mouse model bearing an oncogenic mutated form of KRAS. We obtained the immunocompromised NSG mice models engrafted with patient-derived tumours from the PDX Live™ library at The Jackson Laboratory (Model ID: TM00302). First, we validated the expression of SCAT7 in the patient-derived tumours that were engrafted into the animals by analysing the RNA-seq data of the original early-passaged tumours provided confidentially by The Jackson Library. Next, following the development of the tumours, we performed an LNA therapeutic intervention over a period of 15 days to assess the growth of the tumours in vivo. Interestingly, the PDX mice models injected with SCAT7 LNA-1 exhibited a significant reduction in the growth rate as well as the volumes of the engrafted tumours (FIGS. 6a-c).

These results collectively show that SCAT7 is an oncogenic lncRNA and can be used as a therapeutic target in the treatment of different cancers.

Example 8

Figure 7:
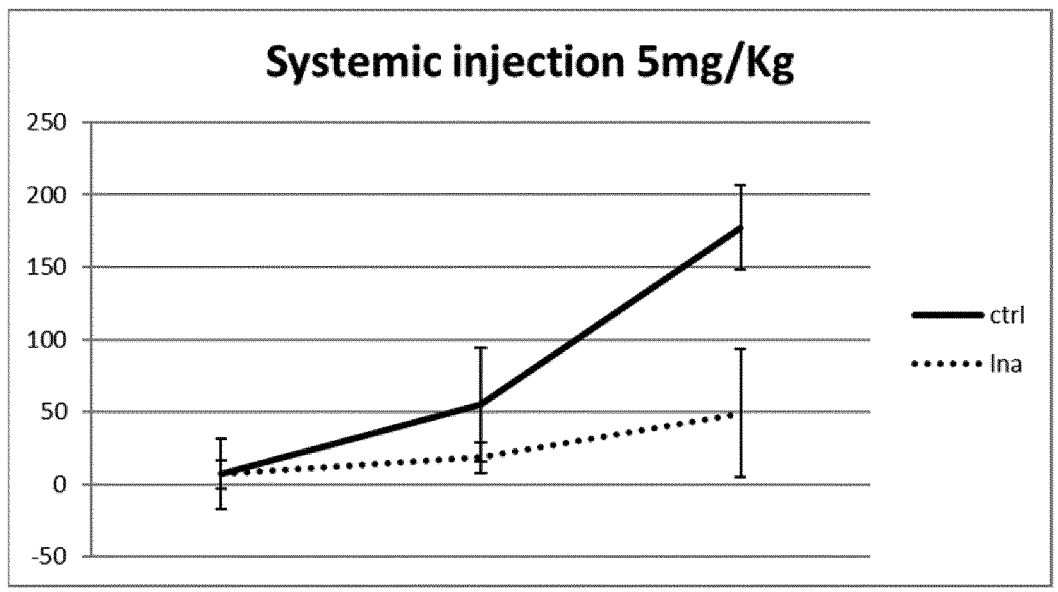
FIG. 7 shows tumor growth rate in mice following systemic injection.

Lung adenocarcinoma A549 xenografts were generated by injecting $1 \times 10^6$ cells in the right flank of 4 weeks old NSG female mice. When tumors became palpable a therapeutic regiment was started comprising injecting 100 μl of CTRL LNA or SCAT7 LNA1 in PBS intraperitoneally two times a week for two weeks. Tumors were measured every 2-3 days and body weight every day. The experiment was terminated when the tumors reached 1 cm² size or lost 10% of their body weight. Systemic injection of SCAT7 LNA1 drastically reduced the tumor growth rate (FIG. 7).

Example 9

Figure 8A:
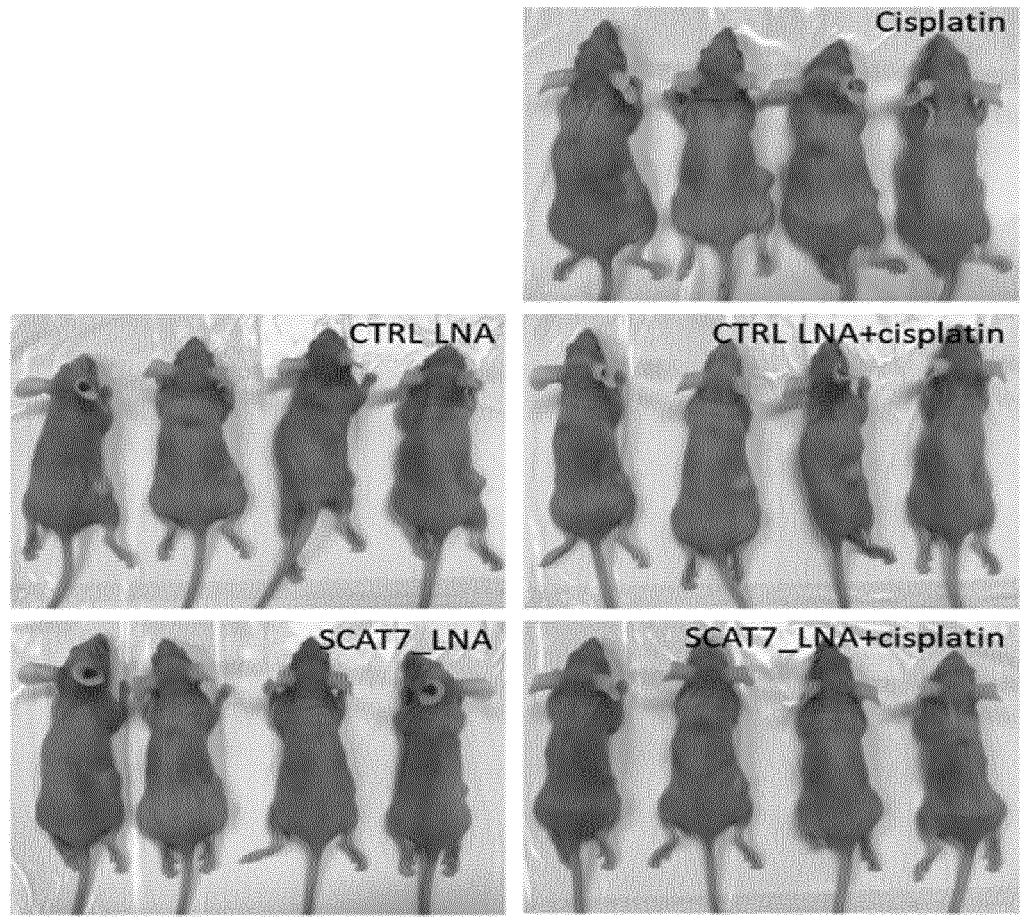
FIG. 8a and FIG. 8b shows treatment of cisplatin-resistant tumors.
Figure 8B:
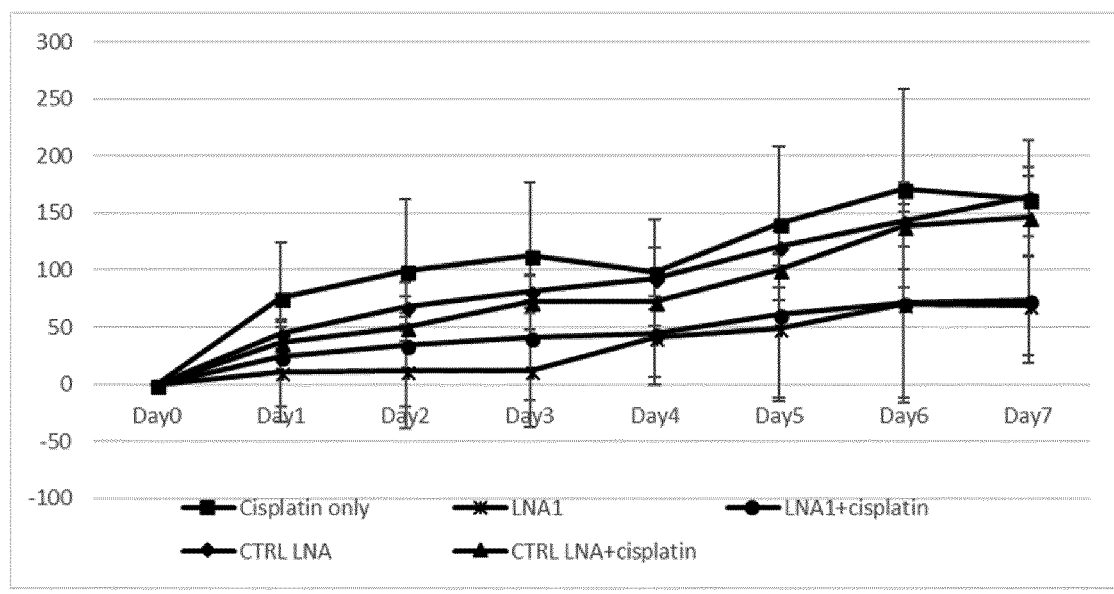

We generated Balb/c nude xenografts by subcutaneously injecting A549/cDDP (cDDP: cisplatin resistant cells) cells to evaluate the response of resistant tumors to cisplatin therapy in association with SCAT7 inhibition. When tumors became measurable a therapeutic regimen was started based on LNA/cisplatin co-treatment with subcutaneous peritumoral injection of cisplatin at 5 mg/Kg and LNA targeting SCAT7 or CTRL LNA. As expected, cisplatin treatment did not affect tumor growth, similarly to subcutaneous injection of CTRL LNA treatment alone and CTRL LNA with cisplatin. However, a significant reduction of tumor growth in xenografts injected with SCAT7 targeting LNA was observed, FIGS. 8a and 8b. Interestingly, presence of cisplatin did not significantly affect the tumour growth both in vitro and in vivo, indicating that SCAT7 knockdown alone is responsible for the reduced tumor growth in A549/cDDP cells.

SEQUENCE LISTING

<160> NUMBER OF SEQ ID NOS: 23

<210> SEQ ID NO 1
<211> LENGTH: 788
<212> TYPE: RNA
<213> ORGANISM: Homo sapiens
<220> FEATURE:
<223> OTHER INFORMATION: >ENST00000419190.1

<400> SEQUENCE: 1

```
cacggggcac uggccugggc agguggcggg aacguugcug ggguggcau cugugcuuuc    60 ggcugcccuc uggcccagga aauuccuccc aggggccagg ccagagaugg gccaggcagg   120
gggagggcaa gugagggaac augaaccccu ggcugaccug agucagaaag cugcuggccc   180
cuaaauucca gagauucagc aacaaagagg ccuaguaggg agaggaguua cuagguuuag   240
ggguuuuucc cagaacaccc aggacucugg ccaggggcug gaaggugcuc caggcucaau   300
gcugggcaau acucauggau uaauggugc uggcugggcc ugccagccua gucguggccc    360 caggguccc acuaaagggc uccuucucca gcgcccacuc uguuggcaag gucuucacua    420
ccaucaccug ccuggacucc auccaagcau caggguugcu gcagucgcuc cugaagagac   480
```

```
ccggcucugc uugaaaguuc uucccucagc gccugcugga gcccucccug ccggaguugc    540
cagaauccac acggaaucca cagaucugcc cugaugauca ugaaggaaug cgaaagagcc    600
ugguaaaacg auauggacuu gugcaaaugc aaagcaaugg ugaagucauc acgaaccgca    660
cagacuggac agaacccuua ucuggcugca auggcugggu ucagucagcc caggggcca    720 gagaauuggc uacaaagagc ucuggagugc ccucccucc aaauaaagua uucuaagcgu    780
gcacugau                                                             788

<210> SEQ ID NO 2
<211> LENGTH: 500
<212> TYPE: RNA
<213> ORGANISM: Homo sapiens
<220> FEATURE:
<223> OTHER INFORMATION: >ENST00000415582.

<400> SEQUENCE: 2
aagagaucag aauucagcuu ccccagggac agcaaggcca agaagguguc cagauccugg     60
ccucucucca gaucuuggac ucucucaagg ccaagacucu cucucuuaag aucucuaucu    120
caaggccaag aucucucucc agauauuggc cucucucaag guacuuccaa gaucucagag    180
ggccauucac ugugaaucua auaugaagac agagaaacca gccuuccaga ggagcggaca    240
cauuuccuua gucccaggau acacuuugug uggaauccac agaucugccc ugaugaucau    300
gaaggaaugc gaaagagccu gguaaaacga uauggacuug ugcaaaugca aagcaauggu    360
gaagucauca cgaaccgcac agacuggaca gaacccuau cuggcugcaa uggcuugggu    420
ucagucagcc caggggccag agaauuggcu acaaagagcu cuggagugcc ccucccuca    480 aauaaaguau ucuaagcgug                                                500

<210> SEQ ID NO 3
<211> LENGTH: 229
<212> TYPE: RNA
<213> ORGANISM: Homo sapiens
<220> FEATURE:
<223> OTHER INFORMATION: Overlapping region

<400> SEQUENCE: 3
ggaauccaca gaucugcccu gaugaucaug aaggaaugcg aaagagccug guaaaacgau     60
auggacuugu gcaaaugcaa agcaauggug aagucaucac gaaccgcaca gacuggacag    120 aacccuauc uggcugcaau ggcuugggu cagucagccc aggggccaga gaauuggcua    180
caaagagcuc uggagugccc cucccuccaa auaaaguauu cuaagcgug                229

<210> SEQ ID NO 4
<211> LENGTH: 16
<212> TYPE: DNA
<213> ORGANISM: Artificial Sequence
<220> FEATURE:
<223> OTHER INFORMATION: LNA 1
<220> FEATURE:
<221> NAME/KEY: misc_feature
<222> LOCATION: 1
<223> OTHER INFORMATION: /note="There are methylene bridges between the
      2' oxygen and the 4' carbon of the nucleotides in positions 1, 2,
      3, 14, 15, 16."

<400> SEQUENCE: 4
cagtgcacgc ttagaa                                                     16

<210> SEQ ID NO 5
```

```
<211> LENGTH: 16
<212> TYPE: DNA
<213> ORGANISM: Artificial Sequence
<220> FEATURE:
<223> OTHER INFORMATION: LNA 2
<220> FEATURE:
<221> NAME/KEY: misc_difference
<222> LOCATION: 1
<223> OTHER INFORMATION: /note="There are methylene bridges between the
      2' oxygen and the 4' carbon of the nucleotides in positions 1, 2,
      3, 14, 15, 16."

<400> SEQUENCE: 5
gtgcacgctt agaata                                                    16

<210> SEQ ID NO 6
<211> LENGTH: 60
<212> TYPE: RNA
<213> ORGANISM: Artificial Sequence
<220> FEATURE:
<223> OTHER INFORMATION: Short hairpin 1

<400> SEQUENCE: 6
gauccggauc ugcccugaug aucaugauca agagucauga ucaucagggc agaucuuuug    60

<210> SEQ ID NO 7
<211> LENGTH: 62
<212> TYPE: RNA
<213> ORGANISM: Artificial Sequence
<220> FEATURE:
<223> OTHER INFORMATION: Short hairpin 2

<400> SEQUENCE: 7
gauccggaua uggacuugug caaaugcuca agaggcauuu gcacaagucc auaucuuuuu    60
ug                                                                   62

<210> SEQ ID NO 8
<211> LENGTH: 21
<212> TYPE: DNA
<213> ORGANISM: Artificial Sequence
<220> FEATURE:
<223> OTHER INFORMATION: combined DNA/RNA molecule (TT overhang); siRNA1
      sense

<400> SEQUENCE: 8
cacagacugg acagaacuct t                                              21

<210> SEQ ID NO 9
<211> LENGTH: 21
<212> TYPE: DNA
<213> ORGANISM: Artificial Sequence
<220> FEATURE:
<223> OTHER INFORMATION: /note="combined DNA/RNA molecule"
      /note="siRNA 1 antisense"

<400> SEQUENCE: 9
gaguucuguc cagucugugt t                                              21

<210> SEQ ID NO 10
<211> LENGTH: 21
<212> TYPE: DNA
<213> ORGANISM: Artificial Sequence
<220> FEATURE:
<223> OTHER INFORMATION: /note="combined DNA/RNA molecule"
      /note="siRNA 2 sense"

<400> SEQUENCE: 10
```
gccagagaau uggcuacaat t                                              21

<210> SEQ ID NO 11
<211> LENGTH: 21
<212> TYPE: DNA
<213> ORGANISM: Artificial Sequence
<220> FEATURE:
<223> OTHER INFORMATION: /note="combined DNA/RNA molecule"
      /note="siRNA 2 antisense"

<400> SEQUENCE: 11
uuguagccaa uucucuggct t                                              21

<210> SEQ ID NO 12
<211> LENGTH: 21
<212> TYPE: DNA
<213> ORGANISM: Artificial Sequence
<220> FEATURE:
<223> OTHER INFORMATION: /note="combined DNA/RNA molecule"
      /note="siRNA 3 sense"

<400> SEQUENCE: 12
cccugaugau caugaaggat t                                              21

<210> SEQ ID NO 13
<211> LENGTH: 21
<212> TYPE: DNA
<213> ORGANISM: Artificial Sequence
<220> FEATURE:
<223> OTHER INFORMATION: /note="combined DNA/RNA molecule"
      /note="siRNA 3 antisense"

<400> SEQUENCE: 13
uccuucauga ucaucagggt t                                              21

<210> SEQ ID NO 14
<211> LENGTH: 16
<212> TYPE: RNA
<213> ORGANISM: Homo sapiens

<400> SEQUENCE: 14
ttctaagcgt gcactg                                                    16

<210> SEQ ID NO 15
<211> LENGTH: 16
<212> TYPE: RNA
<213> ORGANISM: Homo sapiens

<400> SEQUENCE: 15
tattctaagc gtgcac                                                    16

<210> SEQ ID NO 16
<211> LENGTH: 21
<212> TYPE: RNA
<213> ORGANISM: Homo sapiens

<400> SEQUENCE: 16
gatctgccct gatgatcatg a                                              21

<210> SEQ ID NO 17
<211> LENGTH: 21
<212> TYPE: RNA
<213> ORGANISM: Homo sapiens

<400> SEQUENCE: 17
gatatggact tgtgcaaatg c                                              21

<210> SEQ ID NO 18
<211> LENGTH: 19
<212> TYPE: RNA
<213> ORGANISM: Homo sapiens

<400> SEQUENCE: 18
gagttctgtc cagtctgtg                                                 19

<210> SEQ ID NO 19
<211> LENGTH: 19
<212> TYPE: RNA
<213> ORGANISM: Homo sapiens

<400> SEQUENCE: 19
gccagagaat tggctacaa                                                 19

<210> SEQ ID NO 20
<211> LENGTH: 19
<212> TYPE: RNA
<213> ORGANISM: Homo sapiens

<400> SEQUENCE: 20
ccctgatgat catgaagga                                                 19

<210> SEQ ID NO 21
<211> LENGTH: 788
<212> TYPE: RNA
<213> ORGANISM: Homo sapiens

<400> SEQUENCE: 21
aucagugcac gcuuagaaua cuuuauuugg agggaggggc acuccagagc ucuuuguagc     60
caauucucug gccccugggc ugacugaacc caagccauug cagccagaua ggaguucugu    120
ccagucugug cgguucguga ugacuucacc auugcuuugc auuugcacaa guccauaucg    180
uuuuaccagg cucuuucgca uuccuucaug aucaucaggg cagaucugug gauuccugugu   240 ggauucugga acuccggca gggagggcuc cagcaggcgc ugagggaaga acuuucaagc    300
agagccgggu cucuucagga gcgacugcag caacccugau gcuggauggu aguccaggca    360
ggugauggua gugaagaccu ugccaacaga gugggcgcug gagaaggagc ccuuuagugg    420 ggacccugggg ccacgacua ggcuggcagg cccagccagc accaauuaau ccaugaguau    480 ugccagcau ugagccugga gaccuuccca gccccuggcc agagucccugg uguucggg      540 aaaaacccccu aaaccuagua acuccucucc cuacuaggcc ucuuuguugc ugaaucucug    600
gaauuuaggg gccagcagcu uucgacucua ggucagccag gggcaugu cccucacuu       660 gccucccccc ugccuggccc aucucuggcc uggccccugg gaggaauuuc cugggccaga    720
gggcagccga aagcacagau gcccacccca gcaacguucc cgccaccugc ccaggccagu    780
gccccgug                                                            788

<210> SEQ ID NO 22
<211> LENGTH: 500
<212> TYPE: RNA
<213> ORGANISM: Homo sapiens

<400> SEQUENCE: 22
cacgcuuaga auacuuuauu uggaggggagg ggcacuccag agcucuuugu agccaauucu     60
cuggccccug ggcugacuga acccaagcca uugcagccag auaggaguuc uguccagucu    120

```
gugcgguucg ugaugacuuc accauugcuu ugcauuugca caaguccaua ucguuuuacc      180
aggcucuuuc gcauuccuuc augaucauca gggcagaucu guggauucca cacaaagugu      240
auccugggac uaaggaaaug uguccgcucc ucuggaaggc ugguuucucu gucuucauau      300
uagauccaca gugaauggcc cucugagauc uggaaguac cuugagagag gccaauaucu       360
ggagagagau cuuggccuug agauagagau cuuaagagag agagucuugg ccuugagaga      420
guccaagauc uggagagagg ccaggaucug gacaccuucu uggccuugcu gucccugggg      480
aagcugaauu cugaucucuu                                                 500

<210> SEQ ID NO 23
<211> LENGTH: 229
<212> TYPE: RNA
<213> ORGANISM: Homo sapiens

<400> SEQUENCE: 23
cacgcuuaga auacuuuauu uggagggagg ggcacuccag agcucuuugu agccaauucu       60
cuggccccug ggcugacuga acccaagcca uugcagccag auaggaguuc uguccagucu      120
gugcgguucg ugaugacuuc accauugcuu ugcauuugca caaguccaua ucguuuuacc      180
aggcucuuuc gcauuccuuc augaucauca gggcagaucu guggauucc                 229
```

The invention claimed is:

1. A method for treatment of a cancer which is resistant to chemotherapy comprising administering to a patient who has the cancer which is resistant to chemotherapy a polynucleotide that is able to bind to and inhibit a long non-coding RNA transcript that comprises or consists of the sequence SEQ ID NO 1 or SEQ ID NO 2 or a sequence that has at least 95% sequence identity to SEQ ID NO 1 or SEQ ID NO 2.

2. The method of treatment of claim 1, wherein the disease is selected from lung cancer, liver cancer, kidney cancer, bladder cancer, breast cancer, prostate cancer and endometrial cancer.

3. The method of claim 1, wherein the polynucleotide comprises or consists of a sequence selected from the group consisting of SEQ ID NO 4 to SEQ ID NO 13.

4. The method of claim 1, wherein the polynucleotide is a DNA antisense polynucleotide selected from SEQ ID NO 4 and SEQ ID NO 5, a shRNA polynucleotide selected from SEQ ID NO 6 and SEQ ID NO 7, or a siRNA polynucleotide which is a duplex of SEQ ID NO 8 and SEQ ID NO 9, a duplex of SEQ ID NO 10 and SEQ ID NO 11 or a duplex of SEQ ID NO 12 and SEQ ID NO 13.

5. The method of claim 1 where the cancer is resistant to an agent selected from the group consisting of actinomycin, all-trans retinoic acid, azacitidine, azathioprine, bleomycin, bortezomib, capecitabine, cisplatin, carboplatin, chlorambucil cyclophosphamide, cytarabine, daunorubicin, dicycloplatin, docetaxel, doxifluridine, doxorubicin, epirubicin, epothilone, etoposide, fluorouracil, gemcitabine, hydroxyurea, idarubicin, imatinib, irinotecan, lipoplatin, mechlorethamine, mercaptopurine, methotrexate, mitoxantrone, nedaplatin, oxaliplatin, paclitaxel, pemetrexed, picoplatin, satraplatin, teniposide, tioguanine, topotecan, valrubicin, vemurafenib, vinblastine, vincristine, vindesine and vinorelbine.

6. The method of claim 1 where the cancer is resistant to a platinum-based or platinum-containing chemotherapeutic agent.

7. The method of claim 1 where the cancer is resistant to an agent selected from the group consisting of: cisplatin, carboplatin, dicycloplatin, lipoplatin, nedaplatin, oxaliplatin, picoplatin, and satraplatin.

8. The method of claim 1 where the cancer is resistant to cisplatin.

* * * * *